Figure 1:
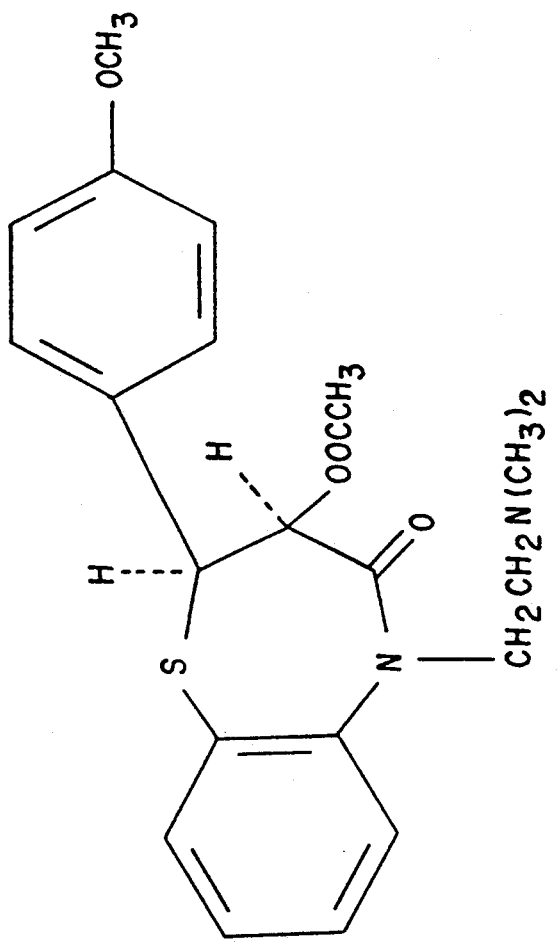

United States Patent [19]
Dodds et al.

[11] Patent Number: 5,274,300
[45] Date of Patent: Dec. 28, 1993

[54] ENZYMATIC HYDROLYSIS OF GLYCIDATE ESTERS IN THE PRESENCE OF BISULFITE ANION

[75] Inventors: David R. Dodds, Millis; Jorge L. Lopez, Framingham, both of Mass.

[73] Assignee: Sepracor, Inc., Marlborough, Mass.

[21] Appl. No.: 309,769

[22] Filed: Feb. 10, 1989

Related U.S. Application Data

[63] Continuation-in-part of Ser. No. 265,171, Oct. 26, 1988, abandoned.

[51] Int. Cl.$^5$ .......................... C12P 7/62; C12P 7/40
[52] U.S. Cl. .................................. 435/280; 435/135; 435/136; 435/155; 435/132
[58] Field of Search ........................................ 435/280

[56] References Cited

U.S. PATENT DOCUMENTS 4,732,853   3/1988   Whitesides et al. ................. 435/123

FOREIGN PATENT DOCUMENTS 0158339   10/1985   European Pat. Off. .
0264457   10/1987   European Pat. Off. .
0343714   11/1989   European Pat. Off. .
0362556   4/1990    European Pat. Off. .

OTHER PUBLICATIONS

Ladner, W. E. and Whitesides, G. M., *J. Am. Chem. Soc.* 1984, 106, 7250-7251.
Philippi, M. Chr. et al., *Biocatalysis in Organic Media* Laane, C. et al. (Eds.) Elsevier Science Publishers B.V., Netherlands (1987), pp. 279-284.
Iriuchijima, et al., *Agric. Biol. Chem.* 1982, 46(6), 1593-1597.
Schneider, M. et al., *Angew. Chem. Int. Ed. Engl.* 1984, 23(1), 64-66, 66 and 67-68.
Ito, Y. et al., *J. Am. Chem. Soc.* 1981, 103, 6739-6741.
Lavayre, J. et al., *Biotech. Bioeng.* 1982, 24, 2175-2197.
Hanada, K. et al., *Agric. Biol. Chem.* 1978, 42(3), 523-528.
Sugita, H. et al., *J. Biochem.* 1980, 87, 339-341.
Tang, J., *Biol. Chem.* 1971, 246(14), 4510-4517.
McCaul, S. and Byers, L. G., *Biochem. Biophys. Res. Commun.* 1976, 72(3), 1028-1034.
Sabbioni, *J. Org. Chem.*, 1987, 52:4565-4570.

*Primary Examiner*—Sam Rosen
*Attorney, Agent, or Firm*—Pennie & Edmonds

[57] ABSTRACT

This invention relates to a method for the production of (2R,3S)-3-(4-methoxyphenyl)glycidic acids and esters thereof, which are synthetic intermediates for the production of the calcium antagonist diltiazem. The method involves the stereoselective enzymatic ester hydrolysis of racemic trans-3-(4-methoxyphenyl)glycidic acid ester to yield the resolved 2R,3S compound as the ester. Membrane reactor methods and apparatus for the conduct of this enzymatic resolution process are also disclosed herein, as is the use of bisulfite anion in the aqueous reaction phase as a means of minimizing the inhibitory effect of an aldehyde reaction by-product on the reaction's progress.

106 Claims, 10 Drawing Sheets

TRANS-3-(4-METHOXYPHENYL) GLYCIDIC ACID ESTER.

CIS-3-(4-METHOXYPHENYL) GLYCIDIC ACID ESTER

MULTIPHASE/EXTRACTIVE MEMBRANE BIOREACTOR FOR ENZYMATIC RESOLUTION OF A DILTIAZEM PRECURSOR

MULTIPHASE / EXTRACTIVE MEMBRANE BIOREACTOR FOR ENZYMATIC RESOLUTION OF A DILTIAZEM PRECURSOR

ENZYMATIC HYDROLYSIS OF GLYCIDATE ESTERS IN THE PRESENCE OF BISULFITE ANION

The present application is a continuation-in-part of a copending application Ser. No. 265,171 entitled "Process for Preparing Optically Active Glycidate Esters," filed Oct. 26, 1988, now abandoned, and incorporated by reference herein in its entirety.

Figure 5:
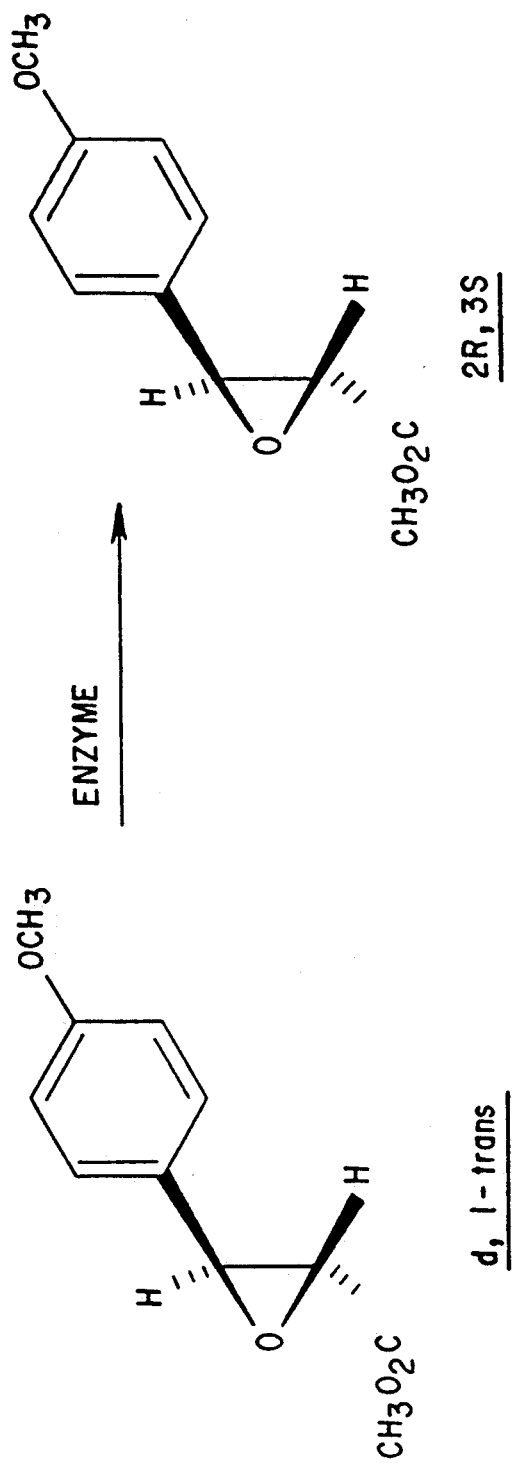

TABLE OF CONTENTS 5 1.0 INTRODUCTION
2.0 BACKGROUND OF THE INVENTION
  2.1 Diltiazem and Its Analogues
  2.2 The Stereochemistry of Diltiazem and Its Precursors
  2.3 Techniques for Resolution of Glycidate Esters
  2.4 Enzymatic Resolution of Racemic Mixtures
3.0 SUMMARY OF THE INVENTION
4.0 BRIEF DESCRIPTION OF THE FIGURES
5.0 DETAILED DESCRIPTION OF THE INVENTION
  5.1 Multiphase Enzymatic Reaction Processes
  5.2 Examples of Multiphase Enzymatic Resolutions
    5.2.0 Procedures for Examples 1-6
    5.2.1 Example 1—Stereoselective Hydrolysis of trans-3-(4-Methoxyphenyl)glycidic Acid Methyl Ester in tert-Butyl Methyl Ether
    5.2.2 Example 2—Stereoselective Hydrolysis of trans-3-(4-Methoxyphenyl)glycidic Acid Methyl Ester in Toluene
    5.2.3 Example 3—Stereoselective Hydrolysis of trans-3-(4-Methoxyphenyl)glycidic Acid Ethyl Ester in tert-Butyl Methyl Ether
    5.2.4 Example 4—Stereoselective Hydrolysis of trans-3-(4-Methoxyphenyl)glycidic Acid n-Butyl Ester in tert-Butyl Methyl Ether
    5.2.5 Example 5—Stereoselective Hydrolysis of trans-3-(4-Methoxyphenyl)glycidic Acid Isopropyl Ester in tert-Butyl Methyl Ether
    5.2.6 Example 6—Stereoselective Hydrolysis of trans-3-(4-Methoxyphenyl)glycidic Acid Isobutyl Ester in tert-Butyl Methyl Ether
    5.2.7 Effect of Cosolvent on Apparent Enantioselectivity E: Example 7
    5.2.8 Effect of Water-Immiscible Organic Solvent on Apparent Enantioselectivity E: Example 8
    5.2.9 Effect of pH on Enzyme Enantioselectivity E: Example 9
    5.2.10 Methyl Ester Hydrolysis Catalyzed by Lipase MAP—Examples 10 and 11
    5.2.11 Methyl Estere Hydrolysis Catalyzed by Lipase OF—EXAMPLE 12
    5.2.12 Resolution of Racemic Methyl 3-(4-Methoxyphenyl)glycidiate in a Membrane Reactor at pH 7—Example 13
    5.2.13 Resolution of Racemic Methyl 3-(4-Methoxyphenyl)glycidiate in a Membrane Reactor at pH 8—Examples 14-17
  5.3 Management of the Aldehyde Byproduct by Adduct Formation with Bisulfite Anion
  5.4. Examples Pertinent to Bisulfite Utilization
    5.4.0 Resolution of Glycidic Acid Methyl Ester in a Multiphase Membrane Reactor
    5.4.1 Example 18
    5.4.2 Example 19
    5.4.3 Example 20
    5.4.4 Example 21
    5.4.5 Example 22
    5.4.6 Example 23
    5.4.7 Example 24
    5.4.8 Example 25
    5.4.9 Example 26
    5.4.10 Example 27

1.0. INTRODUCTION

The esters of trans-3-(4-methoxyphenyl)glycidic acid have utility as precursors in the chemical synthesis of diltiazem. Moreover, these compounds present a very attractive point in the overall synthetic route to diltiazem at which to introduce the desired stereochemistry into the diltiazem precursors through resolution of the racemic glycidic esters and use of the correct, optically purified precursor ester. The present invention pertains to a novel enzymatic method for resolving a racemic mixture of esters of the (2R,3S)- and (2R,3S)-enantiomers of trans-3-(4-methoxyphenyl)glycidic acid. It also pertains to a process for diltiazem production incorporating this resolution step and to membrane reactor means for improving the efficiency of enzymatic resolution of this diltiazem intermediate. Additionally, amelioration of the effects of an inhibitory aldehyde by-product of the reaction process by means of its formation of an adduct with bisulfite anion provided in the aqueous reaction phase is an important aspect of the present invention disclosed herein.

2.0. BACKGROUND OF THE INVENTION

2.1. Diltiazem and Its Analogues

Diltiazem, the chemical structure of which is shown in FIG. 1, is an optically active pharmaceutical compound. More specifically, diltiazem, the chemical name of which is (+)-5-[2-(dimethylamino)ethyl]-cis-2,3-dihydro-3-hydroxy-2-(p-methoxyphenyl) -1,5-benzothiazapin-4(5)-one acetate (ester), consists of a substituted benzothiazapene wherein both chiral carbon atoms have the S absolute stereo-configuration (H. Inoue et al., U.S. Pat. No. 3,562,257). Diltiazem has proven useful for the treatment of angina due to coronary artery spasm, and for exertional angina. The beneficial therapeutic effects achieved with diltiazem are believed to be derived from the inhibition of calcium ion influx during depolarization of the cell membrane in both cardiac and smooth muscle. Diltiazem is known to prevent coronary artery spasm, both spontaneous and ergonovine provoked, and to decrease peripheral vascular resistance. Diltiazem is marketed by Tanabe and by Marion Laboratories in the United States, where it is sold under the tradename Cardizem ®. Analogues to diltiazem are also known to exist, e.g., wherein the benzothiazapene moiety has a single chlorine substituent on the aromatic ring.

Figure 2:
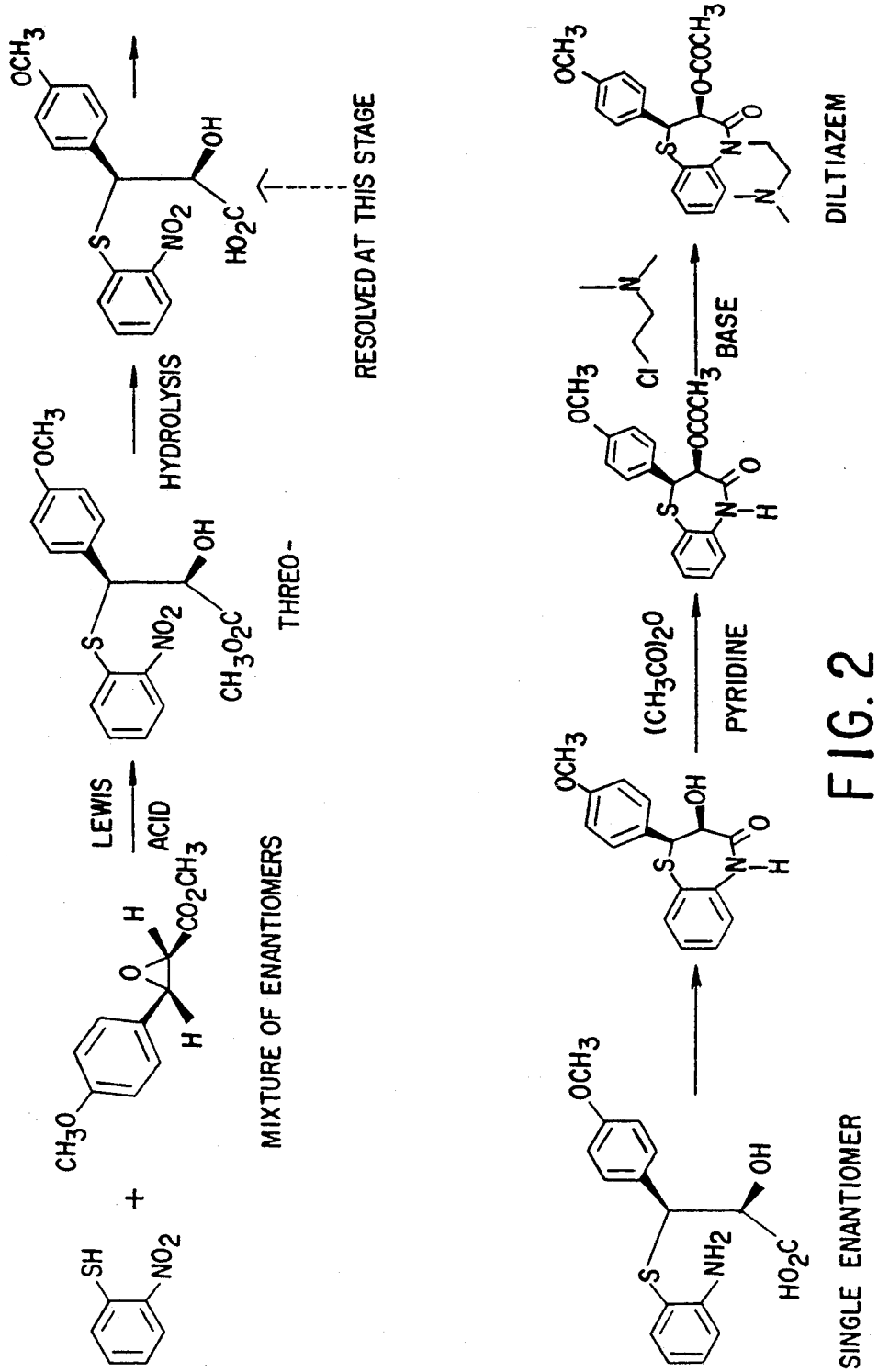

Diltiazem is currently being manufactured via a process similar to that shown in FIG. 2. The first step in the synthetic sequence involves the Lewis acid-catalyzed nucleophilic attack of o-nitrothio- phenol on methyl trans-3-(4-methoxyphenyl)glycidate, as a mixture of enantiomers, to give the threo- compound shown (H. Inoue et al., J. Chem. Soc. Perkin Trans. I, 1725 (1984); H. Inoue et al., J. Chem. Soc. Perkin Trans. I, 421 (1985); H. Inoue et al., U.S. Pat. No. 4,420,628). This threo- compound then needs to be resolved at a subsequent step in the synthetic pathway in order to arrive at the optically active final product (diltiazem).

Alternative production routes to diltiazem utilize o-aminothiophenol in place of o-nitrothiophenol in the step involving opening of and addition to the oxirane ring (S. Nagao et al., U.S. Pat. No. 4,416,819). Such alternative processes also utilize methyl trans-3-(4-methoxyphenyl)glycidate as an intermediate, and thus are subject to improvement by the process of the present invention.

2.2. The Stereochemistry of Diltiazem and Its Precursors

It is known that the above pharmacological effects reside in only one of the two enantiomers of the diltiazem, namely, the d-enantiomer (Merck Index, 10th Edition, 1986, p. 466; Physician's Desk Reference, 41st Edition, 1987, p. 1173). Thus, there is a need to produce diltiazem with the correct stereochemistry, and to introduce such correct stereochemistry at an efficient point in the overall synthesis by production of an optically purified and stereochemically correct intermediate or precursor. As discussed above, diltiazem can be produced from a 3-(4-methoxyphenyl)glycidic acid ester intermediate. At the present time, this intermediate is used in its racemic form, i.e., it is not optically active.

Figure 3:
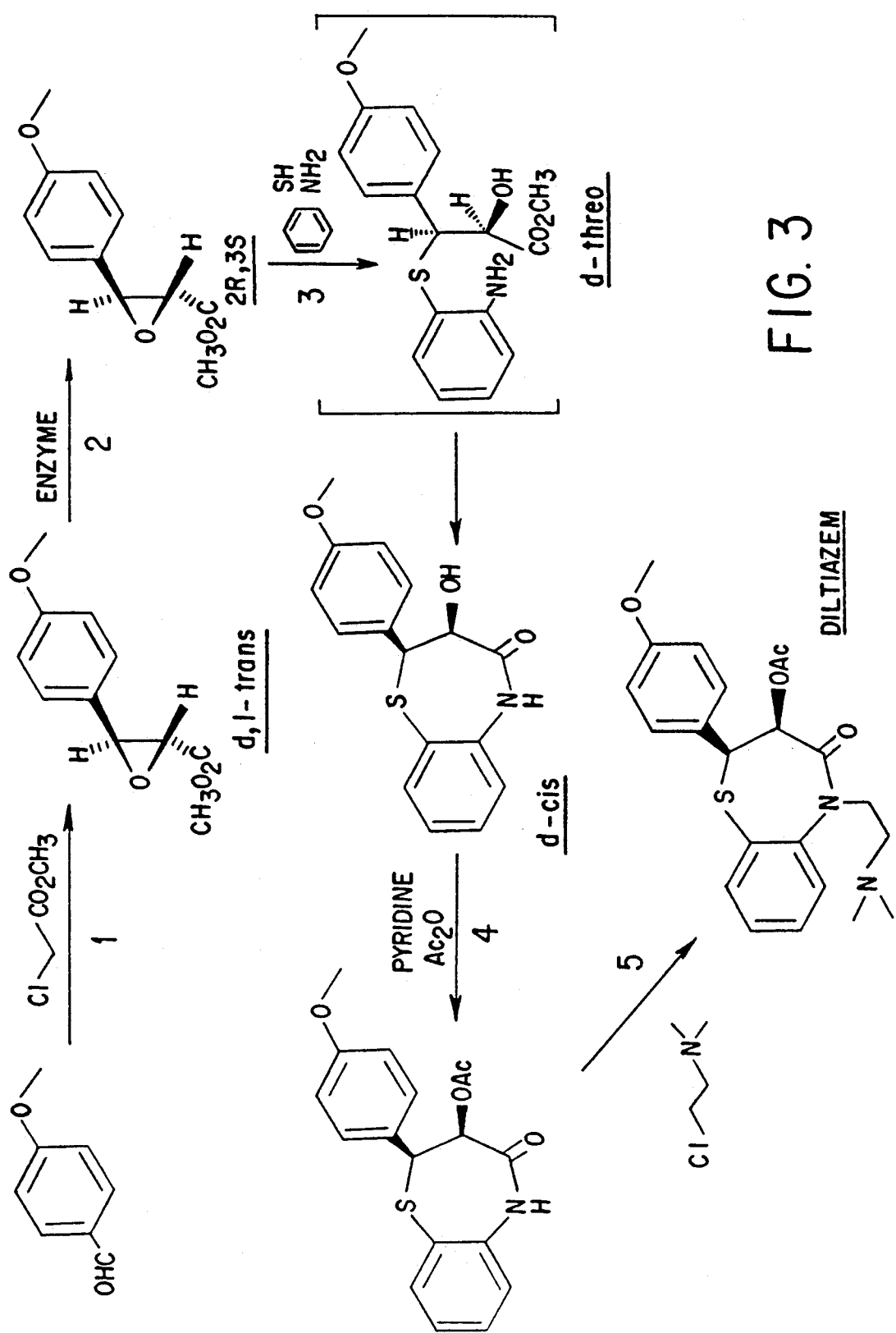

The 3-(4-methoxyphenyl)glycidic acid ester, shown in FIG. 3, contains two chiral centers at carbon atoms 2 and 3, both of which may assume either the R or S absolute configurations. Generally speaking, molecules containing n chiral centers and having no elements of reflective symmetry, will have $2^n$ stereoisomers. In a molecule with 2 chiral centers, there will thus be $2^2$ or 4 stereoisomers. Furthermore, in the case of a molecule having only two chiral centers, these four stereoisomers will be related as a diastereomeric pair of enantiomers, that is two diastereomers each existing as a mixture of its two enantiomers. In the specific case of 3-(4-methoxyphenyl) glycidic acid esters, the two diastereomeric forms are described as cis and trans isomers. The cis isomer is defined as the diastereomer in which the two hydrogen atoms bonded to the carbon atoms of the oxirane ring, that is carbon atoms 2 and 3, eclipse each other, that is, are on the same side of the plane defined by the oxirane ring substructure of the molecule. The trans isomer is defined as the diastereomer in which the hydrogen atoms bonded to carbon atoms 2 and 3 lie on opposite sides of the plane of the oxirane ring. Thus the relative configurations of carbon atoms 2 and 3 are fixed in each diastereomer, although each diastereomer will still exist as a pair of enantiomers. Because diastereomeric compounds are physically distinct entities, not related by symmetry operations performed on the entire molecule, they are physically distinguishable and may be produced separately by the appropriate conventional chemical methods.

The thermodynamically favorable trans diastereomer of a given 3-(4-methoxyphenyl)glycidic acid ester can be synthesized via the Darzen's glycidic ester condensation, and rendered free of any cis diastereomer by conventional purification methods. The trans diastereomer exists in two enantiomeric forms, one having absolute configuration R at carbon atom 2, and absolute configuration S at carbon atom 3. This enantiomer is described as the (2R,3S) isomer. The other enantiomer of the trans diastereomer will have absolute configuration (2S,3R). The enantiomers of the cis diastereomer exhibit absolute configurations (2S,3S) and (2S,3R). The particular glycidic ester enantiomer having absolute configuration (2R,3S) is the compound desired as an optically purified synthetic precursor to diltiazem.

2.3. Techniques for Resolution of Glycidate Esters

The production of (2R,3S)-3-(4-methoxyphenyl)glycidic acid methyl ester has previously been achieved through two fundamentally different procedures. The first procedure involves the synthesis of the chiral glycidic acid methyl ester from achiral precursors, with the creation of chirality during a specific reaction which utilizes a chiral oxidation reagent. Thus, trans-cinnamyl alcohol is asymmetrically epoxidized to give the desired oxirane ring structure, with the correct stereochemistry being created at carbon atoms 2 and 3 simultaneously (K. Igarashi et al., U.S. Pat. No. 4,552,695).

The second procedure, which is generally considered more classical, involves the use of an optically pure reagent used in stoichiometric quantities, to form diastereomeric adducts with the enantiomers of racemic esters or salts of trans-3-(4-methoxyphenyl)glycidic acid (M. Hayashi et al., Japan Kokai Tokkyo Koho JP 61/145160 A2 [86/145160] (1986); M. Hayashi et al., Japan Kokai Tokkyo Koho JP 61/145160 A2 [86/145160] (1986)). These adducts are physically distinguishable, and may be separated by conventional procedures such as fractional crystallization. The thus separated adducts are then decomposed under controlled conditions to leave the separated enantiomers, and the recovered resolving reagent.

Both of these procedures suffer drawbacks, however. In particular, the first procedure involves the use of an unusual catalyst, namely, dialkyl tartrate titanium(IV) isopropoxide, which requires anhydrous conditions and concomitant handling procedures (K. B. Sharpless et al., J. Amer. Chem. Soc., 102 (1980) 5974; K. B. Sharpless et al., Pure Appl. Chem., 55 (1983) 589). More importantly, the reaction which creates the desired stereochemistry does not produce the methyl ester directly. Two further reactions are required beyond the point at which chirality is introduced, involving the production (by oxidation of the alcohol) and esterification of the glycidic acid itself, which is an unstable compound requiring special handling. The second procedure suffers from the need for stoichiometric quantities of previously resolved chiral materials or resolving agents such as alpha-methylbenzylamine (S. Nagao et al., U.S. Pat. No. 4,416,819). Because of the expense of such resolving agents, there also exists a need to recover these materials in a quantitative manner after the resolution step. Additionally, the energy and solvent requirements of large-scale crystallization processes make them unattractive.

2.4. Enzymatic Resolution of Racemic Mixtures

Another approach to the resolution of racemic mixtures of chiral compounds involves subjecting racemic compounds to the enantioselective action of various enzymes. Enzymatic resolution has been widely employed for the lab-scale, preparative-scale, and industrial-scale production of many optically pure compounds including esters but not heretofore the glycidate esters.

Many different classes of enzymes have been used for the resolution of stereoisomers on a preparative scale, including hydrolases (especially the lipases, proteases and esterases such as chymotrypsin), lyases and oxidoreductases (e.g., amino acid oxidases and alcohol reductases). Generally speaking, enzymes for use in resolutions should ideally exhibit broad substrate specificity, so that they will be capable of catalyzing reactions of a wide range of "unnatural" substrates, and they should exhibit a high degree of stereoselectivity for catalyzing the reaction of one isomer to the exclusion of others.

The hydrolases (e.g., lipases, proteases and esterases) are among the more attractive enzymes for use in resolutions, because they are commercially available at reasonable cost, they do not require expensive cofactors, and some of them exhibit reasonable tolerance to organic solvents. Additionally, chiral chemistry often involves alcohols, carboxylic acids, esters, amides and amines with chiral carbons, and carboxyl hydrolases are preferred choices as stereoselective catalysts for reactions of such species [Cambou, B. and A. M. Klibanov, *Biotechnol. Bioeng.*, 26:1449 (1984)]. Many pharmaceuticals and their intermediates exhibit very low solubilities in water, and accordingly a number of enzyme-mediated optical resolutions have been conducted under multiphasic reaction conditions.

Enzymatic treatment has been applied to the resolution of racemic mixtures of amino acid esters. For example, Stauffer [U.S. Pat. No. 3,963,573] produced optically pure N-acyl-L-methionine by treating N-acyl-D,L-methionine ester with microbial proteases and separating the product acid from the reaction mixture. Similarly, Bauer [U.S. Pat. No. 4,262,092] prepared optically pure D-phenylalanine ester by subjecting a racemic mixture of an N-acyl-D,L-phenylalanine ester to the action of a serine protease, separating the unaffected N-acyl-D-phenylalanine ester, and removing the N-acyl and ester groups. Matta et al. [*J. Org. Chem.*, 39:2291 (1974)] used chymotrypsin in the resolution of precursors of the drug 3-(3,4-dihydroxyphenyl)alanine or dopa.

Enzymes have also been explored for the resolution of other compounds such as agricultural chemicals, sometimes in biphasic reactions systems. In particular, Cambou and Klibanov [*Biotech. Bioeng.*, 26:1449 (1984)] examined the use of lipase immobilized in porous beads for the enzymatic resolution of mixtures of (R,S)-2-(p-chlorophenoxy)propanoic acid (whose R isomer is a herbicide) and various esters thereof. The differing solubility properties of the acids and esters used in their studies required the dispersion and agitation of mixtures containing the immobilized solid-phase enzyme, an aqueous buffer, and the water-immiscible organic phase containing solvent and reactant—a relatively inefficient process.

Additional examples can be provided of the state-of-the-art of enzyme-mediated resolution as applied to the production of optically purified pharmaceuticals, albeit not to the enzymatic resolution of diltiazem precursors. Sih (U.S. Pat. No. 4,584,270] has disclosed enzymatic means for the production of optically pure (R)-4-amino-3-hydroxybutanoic acid, a key intermediate in the preparation of L-carnitine. Additionally, certain optically pure D-amino acids (in particular, the D-arylglycines such as phenylglycine and 4-hydroxyphenylglycine) are used as side chains in the manufacture of semisynthetic penicillins and cephalosporins. Schutt et al. [*Biotechnol. Bioeng.*, 27:420 (1985)] have subjected racemic mixtures of such nonpolar N-acyl-D,L-amino acid esters to the hydrolytic action of subtilisin in two-phase systems for the purpose of obtaining optically purified D-amino acids. In still other references, enzymes derived from microorganisms were utilized to resolve esters of naproxen and ibuprofen. C. J. Sih et al. [*Tetrahedron Letters*, 27:1763 (1986)] describes that esters of ibuprofen and naproxen are capable of being stereospecifically resolved using a microorganism-derived lipase.

In summary, there exists a need in the art for more efficient methods for production of optically purified diltiazem and its analogues, and in particular for improved processes for the optical resolution of racemic diltiazem precursors including the esters of trans-3-(4-methoxyphenyl) glycidic acid. Furthermore, while enzymatic resolution techniques have been employed for the production of many optically pure pharmaceuticals and their precursors, this technique has not yet been disclosed and successfully applied to the resolution of the glycidate esters that are chiral intermediates in the production of diltiazem. The present invention provides such an enzymatic resolution method.

3.0. SUMMARY OF THE INVENTION

The resolution process of the present invention is accomplished through the use of an enzyme that preferentially catalyzes hydrolysis of one of the two enantiomers of a given glycidic ester to the parent glycidic acid, leaving intact the enantiomer having the desired absolute configuration as the glycidic ester. A specific embodiment of this invention pertains to hydrolytic enzymes, with particularly preferred enzymes being chosen from the lipases and proteases, capable of preferentially hydrolyzing simple alkyl esters (e.g., the methyl ester) of (2S,3R)-methoxyphenylglycidate at a rate higher than the rate of hydrolysis of the corresponding (2R,3S)-enantiomer of methyl methoxyphenylglycidate, permitting recovery of the latter species in optically purified form for use as an optically resolved intermediate in the production of diltiazem.

Also included in this invention and described herein are methods for the efficient conduct of the enzymatic resolution step, including the use of multiphase and extractive membrane reactors to improve the efficiency of the biocatalytic reaction, as well as the provision of bisulfite anion in the aqueous reaction phase for the purpose of forming an adduct with an otherwise inhibitory and troublesome aldehyde by-product.

4.0. BRIEF DESCRIPTION OF THE FIGURES

This invention may be more readily understood by reference to the following detailed description of the invention and figures:

FIG. 1. is a representation of the chemical structure of the diltiazem molecule.

FIG. 2. is a schematic representation of a prior-art process for the production of diltiazem.

FIG. 3. is a schematic representation of a method for the production of the pharmaceutically active diltiazem stereoisomer based on the use of the optically purified precursor (2R,3S)-3-(4-methoxyphenyl)glycidate methyl ester, said precursor being resolved from the racemic d,l-trans mixture in step 2 of the diagrammed process.

Figure 4:
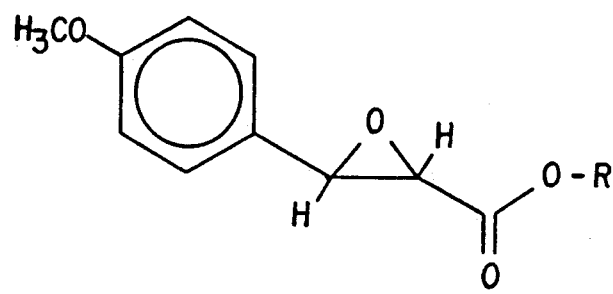
Figure 4:
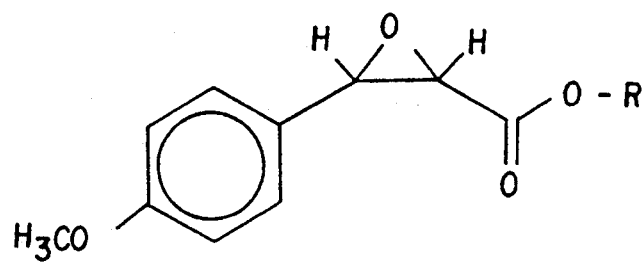

FIG. 4. is a representation of the chemical structures of trans- and cis-isomers of the 3-(4-methoxyphenyl)glycidic acid ester, wherein it is the (2R, 3S)-trans stereoisomer which is particularly preferred for diltiazem manufacture and wherein R denotes the esterified alcohol moiety.

For purposes of clarity, specific stereoisomers with particular absolute configurations about the chiral carbons, and generally the preferred configuration for diltiazem production, are shown in the above figures.

However, it should be noted that current prior-art diltiazem processes such as that shown in FIG. 2 utilize racemic intermediates (e.g., the methyl ester of d,l-trans-3-(4-methoxyphenyl)glycidic acid in the initial steps of the process.

FIG. 5. is a schematic representation of the enzymatic resolution step of the present invention, wherein the two-component racemic mixture of d,l-trans enantiomers of an ester of 3-(4-methoxyphenyl)glycidic acid is subjected to the action of a stereoselective enzyme with the result that the undesired (2S,3R)-enantiomer is preferentially hydrolyzed to the corresponding enantiomer of its parent acid, leaving intact the enantiomer with the desired (2S,3R) absolute configuration in the chemical form of the unreacted ester.

Figure 6:
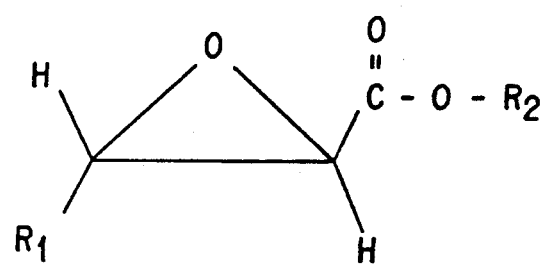

FIG. 6. is a schematic representation of a substituted glycidate ester that is susceptible to enzymatic resolution by the process of the present invention.

Figure 7:
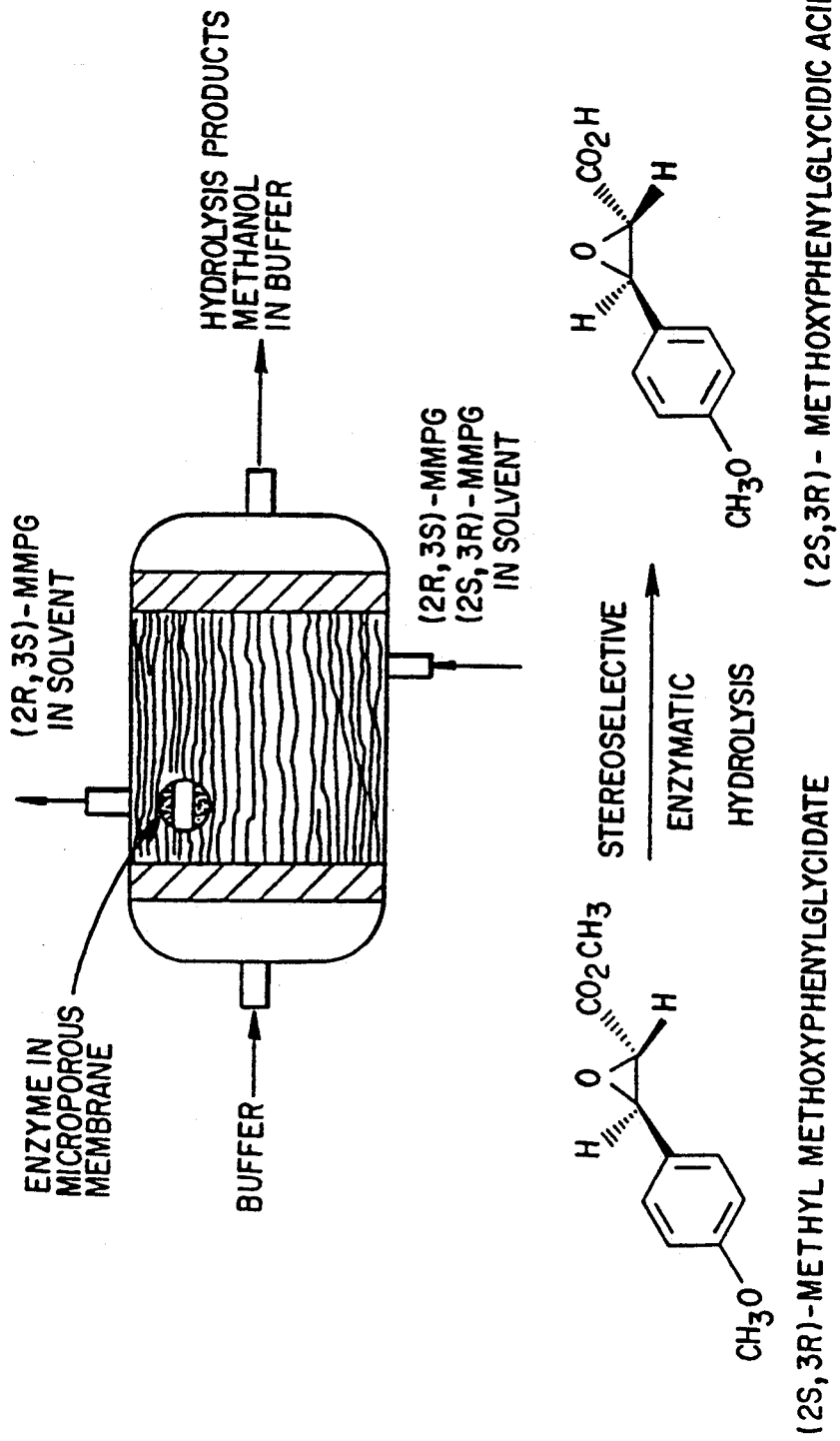

FIG. 7. is a schematic representation of a hollow-fiber multiphase/extractive enzyme membrane reactor with organic-phase feed of the racemic methyl 3-(4-methoxyphenyl)glycidate esters (MMPG), aqueous-phase withdrawal of water-soluble enzymatic reaction products including the (2S,3R)-3-(4-methoxyphenyl)-glycidate salt and its decomposition products, and organic-phase withdrawal of the unreacted and desired (2R,3S)-3-(4-methoxyphenyl)glycidate methyl ester.

Figure 8:
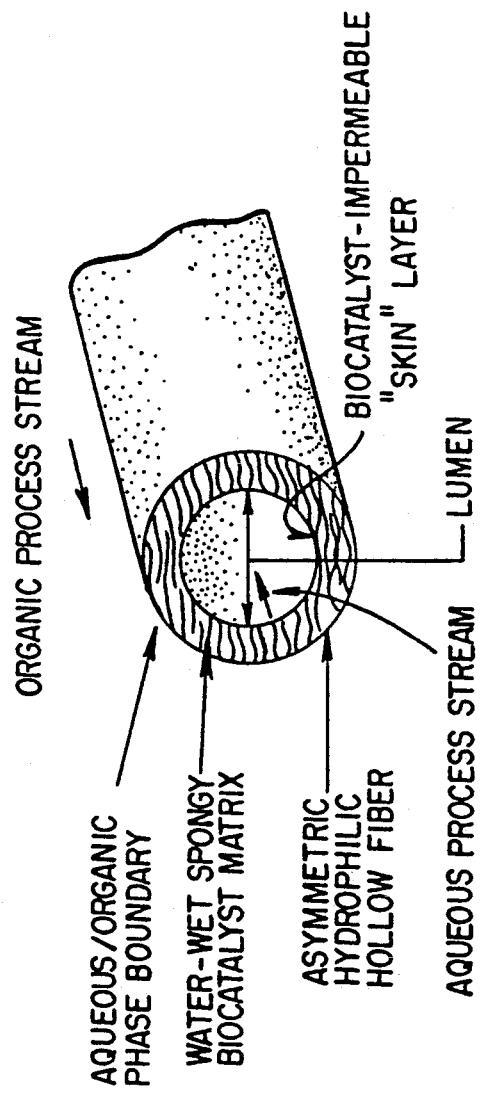

FIG. 8. is a schematic representation of a preferred embodiment of the invention wherein the enzyme is reversibly contained within an asymmetric, hydrophilic, and microporous hollow-fiber membrane.

Figure 9:
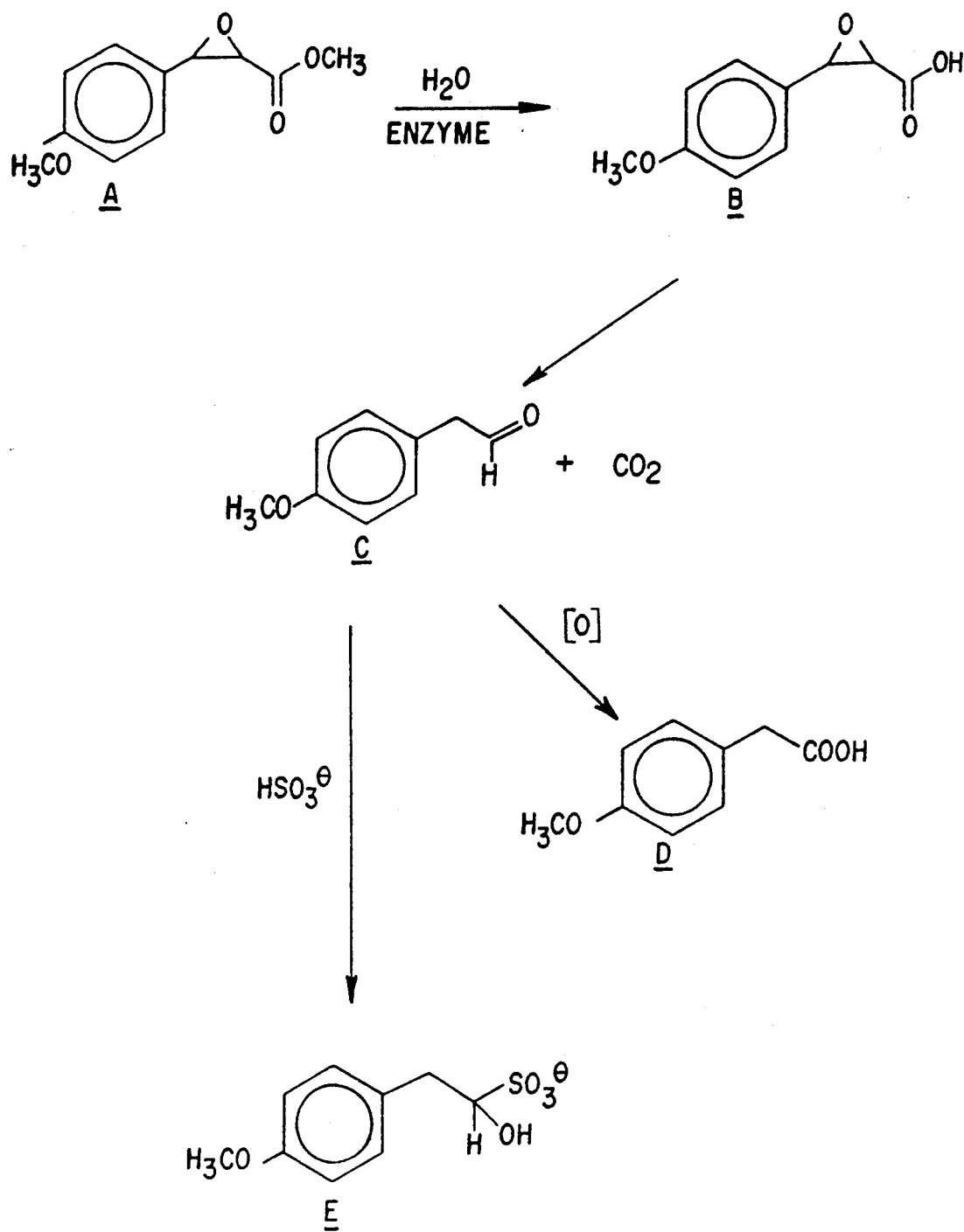

FIG. 9. is a diagram summarizing the chemistry involved in the formation of an aldehyde by-product from its glycidic acid precursor, as well as the chemistry of two subsequent reactions of the aldehyde—namely, adduct formation with bisulfite anion and oxidation.

Figure 10:
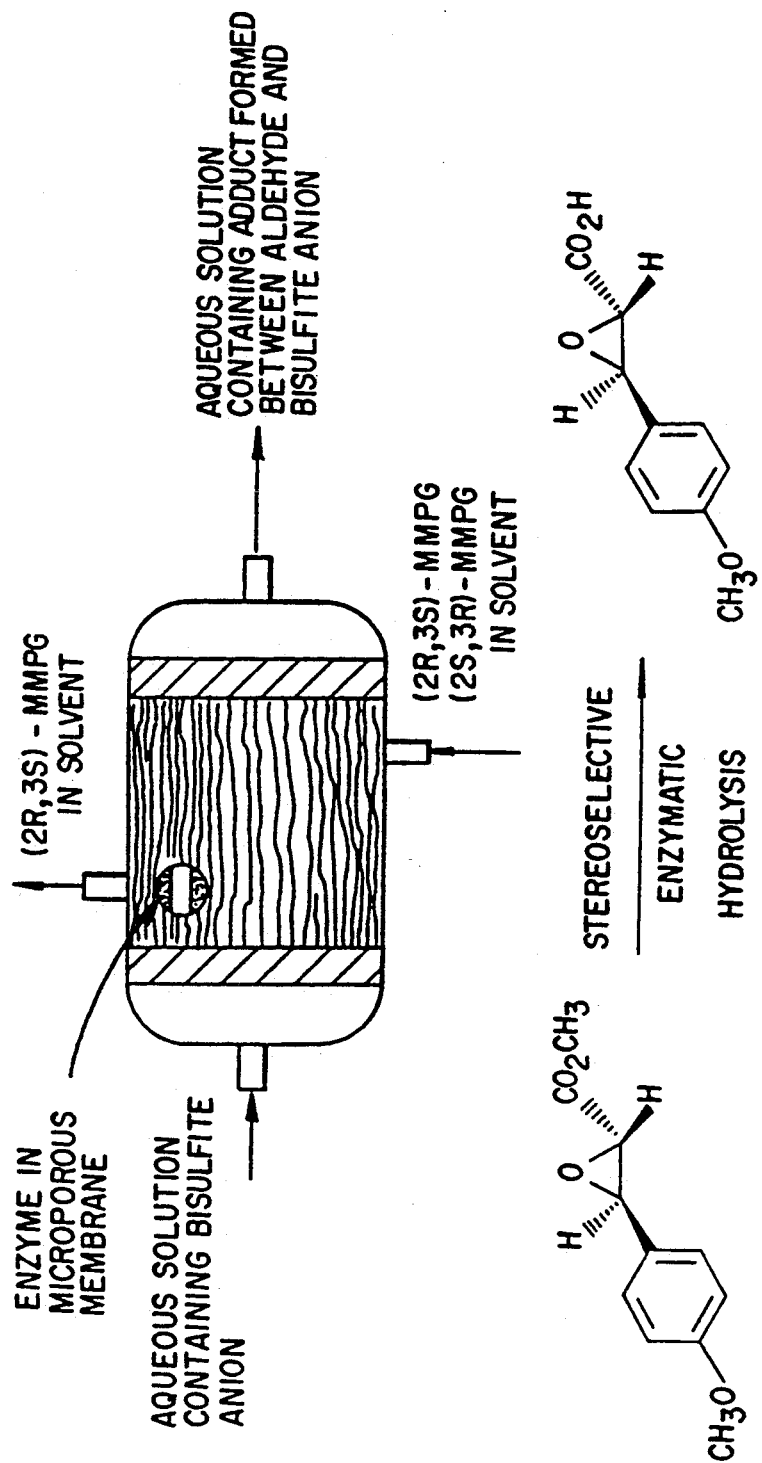

FIG. 10. is a schematic representation of a hollow-fiber multiphase/extractive enzyme membrane reactor supplied with a racemic feed mixture of methyl 3-(4-methoxyphenyl)glycidate esters (MMPG) in a water-immiscible organic solvent on one side of the membrane and an aqueous solution containing bisulfite anion supplied to the opposite side of the membrane. Water-soluble reaction products—notably including the adduct formed by reaction of bisulfite with the inhibitory aldehyde by-product—are shown being withdrawn via the exiting aqueous process stream, while the unreacted and desired (2R-3S)-3-(4-methoxyphenyl)glycidate methyl ester is withdrawn via the exiting organic process stream.

5 0. DETAILED DESCRIPTION OF THE INVENTION

It is an object of the present invention to provide an improved process for the production of resolved glycidic esters, subsequently useful in the synthesis of optically pure diltiazem. Specifically, this invention relates to production of optically pure intermediates, namely (2R,3S)-3-(4-methoxyphenyl)glycidic acid methyl ester and other simple alkyl esters, by enzymatic resolution of a racemic mixture of the d,l-trans esters. This is accomplished in a subtractive resolution process, wherein the undesired (2S,3R)-glycidate ester is enzymatically hydrolyzed and removed from the desired (2R,3S)-enantiomer, with the net result that the latter compound is optically purified in the process.

In a process for diltiazem manufacture, the resolution of threo-2-hydroxy-3-(4-methoxyphenyl)-3-(2-nitrophenylthio)propionic acid methyl ester can be avoided if the glycidic acid ester subject to the initial nucleophilic attack by o-nitrothiophenyl to produce the threo-compound is, itself, optically purified. The enzymatic resolution process of this invention provides means by which to accomplish the enantioselective preparation of the desired optically active intermediate, i.e. a trans-(2R,3S)-3-(4-methoxyphenyl)glycidic acid ester.

It is known that glycidic acids are unstable except under certain conditions; however, the esters of glycidic acids are relatively stable (apart from their hydrolytic instability) and are useful synthetic intermediates. In order to use a glycidic acid ester as a synthetic precursor in the synthesis of diltiazem, and to produce the desired stereochemistry in the final product, the glycidic acid ester with absolute configuration (2R,3S) is required. Thus, a suitable combination of enzyme and glycidic acid ester is required that results in the enzyme-catalyzed hydrolysis of the enantiomer with (2S,3R) absolute configuration, permitting recovery of the enantiomer with absolute configuration (2R,3S) as the unhydrolyzed glycidic ester.

5.1. Multiphase Enzymatic Reaction Processes

The present process for the resolution of glycidic esters is one in which the undesired enantiomer present in the racemic glycidic ester substrate is selectively transformed by hydrolysis of the ester function into a species easily separated from the remaining glycidic ester enantiomer by known physical methods. Specifically, in the case of this invention, the desired ester enantiomer is soluble in organic solvents that are immiscible with water, while at least one of the products of hydrolysis of the undesired glycidic ester has appreciable water solubility. (As the term "immiscible" is used herein, it is meant to encompass solvents which are completely, substantially, or partially immiscible with water—i.e., solvents that form a separate organic phase when placed in contact with water.) The resolution process described herein is a kinetic resolution process in which each enantiomer of the racemic substrate mixture exhibits some susceptibility to enzymatic hydrolysis, but one of said enantiomers is hydrolyzed more rapidly than the other in the presence of an appropriate enzyme catalyst. In this situation, the ability of an enzyme to discriminate between two competitively reacting enantiomers may be quantified by the enantioselectivity value E, as described by C.-S. Chen et al. (J. Amer. Chem. Soc., 104 (1982) 7294). The formula for calculation of E in the case of a subtractive kinetic resolution process is given as follows:

$$E = \{ln[(1-x)(1-ee(S))]/ln[(1-x)(1+ss(S))]\}$$

where x is the degree of conversion of the entire quantity of starting substrate, expressed as a decimal fraction, and ee(S) is the enantiomeric excess of the remaining, non-hydrolyzed substrate enantiomer, also expressed as a decimal fraction. This formula permits comparison of enzyme reactions which have proceeded to different degrees of conversion, in which case direct comparison of the enantiomeric excess of remaining glycidic ester substrate is not possible. It is also possible to use this E value and corresponding calculations to compare the apparent selectivity of the same enzyme operating under varying conditions.

Despite the known inactivating effects of epoxides on enzymes, it is possible as taught by this invention to use enzymes to catalyze the hydrolysis of carboxylic acid esters of the epoxide containing compounds generally known as glycidic acids, in an enantioselective manner. The racemic carboxylic acid esters of the parent glycidic acids include those having the general structure shown in FIG. 6, wherein $R_1$ is a substituent selected from the group of phenyl and substituted phenyl, and $R_2$ is a group derived from an alcohol. The substituted phenyl group may be substituted with various groups including hydroxy, methoxy, phenoxy, benzyloxy, alkoxy, aryloxy, arylalkoxy, and halide. A particularly important $R_1$ group is 4-methoxyphenyl, since it is this group which is pertinent to diltiazem manufacture. The phenyl group substituent may occupy one or more of the ortho, meta, or para positions with respect to the glycidic ester moiety. With regard to the alcohol moiety $R_2$, this group will be selected from the group consisting of straight-chain alkyl with 1 to 8 carbon atoms, branched-chain alkyl with 3 to 8 carbon atoms, substituted alkyl, aryl, substituted aryl, and alkoxyalkyl. Preferred alkyl substituents include methyl, ethyl, isopropyl, and isobutyl, while preferred alkoxyalkyl substituents include the methoxyethyl and ethoxyethyl groups.

The preferred embodiment of this invention corresponds to the case in which $R_1$ is a para-methoxyphenyl group, $R_2$ is a methyl group, the relative configuration of groups $R_1$ and $R_2$ are trans, and the absolute configuration of the desired glycidic acid ester product after enzymatic resolution is (2R,3S). It should be noted that the corresponding cis glycidic ester diastereomer, in which groups $R_1$ and $R_2$ are on the same side of the plane of the epoxide ring, may also be resolved, and the resulting (2S,3S)-cis-3-(4-methoxyphenyl)glycidic acid esters may also be used in the subsequent production of diltiazem.

In the present invention, enzyme catalysts are present either dissolved or dispersed in an aqueous phase. Although the glycidic esters described herein are generally quite insoluble in water, the epoxide ring is susceptible to opening through nucleophilic attack by species such as hydroxide ions and water molecules, even in the absence of enzymes. Exposure of the preferred substrate of this invention, described above, to an aqueous sodium phosphate buffer solution of pH 7.0 for 18 hours at ambient temperature, in the absence of any organic solvent or enzyme preparation, leads to the loss of glycidic ester, and the formation of a water-soluble compound. However, in the presence of toluene in a 1-to-1 phase ratio with the same aqueous phase, there was no loss of glycidic ester over the same period of time, and 100% of the glycidic ester could be recovered by separation and evaporation of the organic phase. Therefore, the use of an organic phase as a method for protecting the substrate from undesired transformations by water, hydroxide ions, or water-soluble buffer systems is a significant aspect of this invention. These experimental observations indicate the need for a biphasic system, and preferably a multiphase/extractive membrane reactor as described below, for efficiently conducting the enzyme-mediated resolution process disclosed herein.

In the present invention, a wide variety of commercially and otherwise available preparations of hydrolytic enzymes can be used directly to perform enantioselective hydrolyses on the glycidic esters represented by the structure in FIG. 6. The enzymes contained in such preparations may be from any of the general classes of hydrolytic enzymes described as esterases, lipases, proteases, peptidases, and acylases. In addition, such preparations may be derived from both eukaryotic and prokaryotic cells, including but not limited to those from the following mammalian sources; porcine liver, porcine pancreas, porcine kidney, and bovine pancreas; the plant source wheat germ; and those from the following microbial genera; Aspergillus, Candida, Geotrichum, Humicola, Mucor, Penicillium, Rhizopus, Streptomyces, Bacillus, Chromobacterium, and Pseudomonas. In preferred embodiments of this invention, commercial preparations containing lipases derived from the microorganisms Mucor *Mucor javanicus, Mucor miehei,* and other Mucor species, *Candida cylindracea, Pseudomonas fluorescens,* and commercial preparations containing the protease known as Protease BPN' from Bacillus so.. are used as hydrolytic catalysts.

Reaction conditions for the enzymatic hydrolysis include the use of a two-phase system, in which the enzyme preparation is dissolved or dispersed in an aqueous phase, and the glycidic ester is dissolved in an organic phase chosen from organic solvents known to be appreciably immiscible with water. The pH of the aqueous phase may range from 5 to 9, according to the pH optimum of the enzyme preparation in use, and provided that the pH chosen does not have a deleterious effect on the glycidic ester. It is desirable to maintain the pH of the aqueous phase within the desired range over the course of the hydrolysis by the use of a buffer system, or an automatic titrator or other pH controlling device. Similarly, the temperature at which the hydrolysis is performed may vary over a wide range, provided that both the aqueous and organic phases remain liquid, the enzyme chosen does not experience denaturation at a rate too rapid to allow its use, and the glycidic ester remains stable. The relative volumes of the aqueous and organic phases are not critical, and may vary over a wide range. Likewise, the concentration of enzyme preparation in the aqueous phase, the concentration of glycidic ester in the organic phase, and the ratio of these concentrations, are not critical and may vary over a wide range. In the preferred embodiment of this invention, the ratio of the organic to aqueous phase, the temperature, the pH of the aqueous phase, and the concentrations of the enzyme preparation in the aqueous phase and the glycidic ester in the organic phase, are chosen to be such that an optimal combination of rate and enantioselectivity of hydrolysis is realized.

Since the racemic glycidic ester substrate is soluble in the organic phase and nearly insoluble in the aqueous phase, the enantiomer of the racemic substrate mixture which is less easily hydrolyzed will be present in the organic phase in a higher concentration than that of the more readily hydrolyzed glycidic ester enantiomer, thus creating an organic solution of the desired glycidic ester enantiomer which increases in the degree of resolution (i.e., enantiomeric excess) as a function of the extent of hydrolysis and the enantioselectivity value E. The extent of hydrolysis of the total racemic glycidic ester substrate may be adjusted to permit the recovery of the desired glycidic ester at any desired level of enantiomeric excess; higher conversions yield organic-phase product esters of increasing optical purity.

In the case of the subtractive resolution process of the present invention, the optimum situation is that in which an enzyme displays an infinitely large E value. In this case, at 50% hydrolysis of the total starting substrate, 100% of the non-hydrolyzed material will remain in the organic phase after reaction at an optical purity of 100% enantiomeric excess. However, if a given enzyme displays a lower E value, the overall extent of hydrolysis must be allowed to proceed past 50%, to an extent that is determined by the formula derived by Chen et al. and reproduced above. Preferably, the enzyme catalyst will be chosen to display the largest E value possible, thus permitting the recovery of the greatest amount of desired glycidic ester enantiomer for a given degree of enantiomeric excess. This material may then be recovered by removing the organic solvent by known methods.

A preferred enzymatic resolution process is conducted in a dispersed-phase system consisting of immiscible aqueous and organic phases vigorously contacted with one another in the presence of enzyme; this can be done in such conventional liquid-liquid contacting equipment as stirred-tank reactors or mixer-settlers. To improve reaction economics, it will be advantageous to immobilize the enzyme on a solid-phase, high-surface-area support in order to facilitate its recovery and reuse, and a process wherein the enzyme is immobilized on particulate supports (e.g., microporous particles, gel-type beads, and ion-exchange resins) is within the scope of the present invention. In such cases, the immobilized enzyme particles may either be dispersed along with the aqueous and organic phases, or they may be packed in a column through which the aqueous and organic phases are made to flow. By the same token, the present invention is not limited to the use of isolated enzymes as biocatalysts, and it will be apparent to those skilled in the art that immobilized whole cells and other microorganism preparations are also within its scope.

An additional and preferred embodiment of the present invention pertains to conducting the enzymatic resolution process within a multiphase/extractive enzyme membrane reactor. Such multiphase and extractive membrane reactors are described by Matson in U.S. Pat. No. a4,800,162, which is incorporated herein by reference. Multiphase enzyme membrane reactors are particularly advantageous in managing reaction-engineering problems associated with an enzyme's substrate, such as its poor water solubility and/or limited hydrolytic stability. Low solubility and stability in water are both characteristics of the glycidic acid esters that are to be resolved by the practice of the present invention. By the same token, extractive enzyme membrane reactors are particularly useful in managing reaction-engineering problems associated with the products of an enzymatic reaction, such as enzyme inhibition (including inactivation) by inhibitory products or limited conversion in reaction processes that are thermodynamically unfavorable or reversible. Again, as demonstrated subsequently in the experimental examples described Section 5.2 and 5.4, product inhibition is a characteristic exhibited by the enzymatic resolution of the glycidic esters of interest here. Thus, multiphase/extractive membrane reactors have considerable utility in improving the efficiency of the enzymatic reaction.

Generally speaking, the enzyme-activated membrane in the membrane reactor process of this invention will typically consist of a porous and hydrophilic (i.e., water-wet) membrane which is suitably activated by incorporation of an appropriate enzyme within it or on one or more of its surfaces by various means. One surface of this enzymatically active membrane is placed in contact with a first process stream, the feed stream, which typically contains a sparingly water-soluble (i.e., water-immiscible) substrate for the enzyme. Typically, this water-immiscible (organic-based) feed stream contains the reactant dissolved in a water-immiscible organic solvent that serves as a carrier fluid.

Concurrently, the second surface of the enzymatically active membrane is contacted with an aqueous process stream which serves one or more of the following purposes: to supply or remove any water of reaction; to provide means for control of reaction pH (and in some cases access to enzyme contained in the membrane); and to provide means for removal of water-soluble and inhibitory reaction products. When properly operated, the aqueous/organic phase boundary will reside at the surface of the water-wet enzyme-activated membrane that is in contact with the water-immiscible organic feed stream, and a substantially aqueous environment will be provided for operation of the enzyme in the hydrophilic, water-wet membrane. Two inlet (i.e., feed) and two outlet (i.e., product) streams will thus be supplied to and removed from the membrane reactor module in the process of this invention, and the membrane reactor module will thus necessarily be configured with two inlet and two exit ports. One inlet/outlet pair of these ports will be devoted to the supply and withdrawal of the organic-phase process stream, while the other pair will be dedicated to supply and removal of the aqueous process stream.

With hydrophilic or water-wet enzyme-activated membranes, this organic process stream is preferably placed under a small positive pressure relative to the aqueous process stream in contact with the opposite surface of the membrane. This resulting small organic-to-aqueous pressure difference across the membrane serves to prevent the ultrafiltrative flow of a portion of the aqueous process stream across the membrane. At the same time, by operating the process in this manner the organic phase will be prevented from intruding into the pores of the water-wet enzyme membrane by the capillary forces acting at the surface of the membrane in contact with it.

In the practice of the invention herein, the poorly water-soluble and hydrolytically unstable reactant is fed to the membrane reactor in a water-immiscible organic process stream, where it is contacted with a first surface of the enzymatically active membrane. Molecules of the reactant subsequently diffuse to the organic/aqueous interface located at the first surface of the membrane, where they partition into aqueous regions of the membrane and undergo enzyme-catalyzed conversion to products. Where at least one of the reaction products exhibits significant water-solubility, and especially where it is much more water-soluble than the reactant, this product species diffuses out of the membrane and into the aqueous process stream in contact with the second surface of the enzymatically active membrane, to be subsequently removed from the reactor.

In summary, the enzyme-activated membrane in this continuous multiphase bioreactor process serves in three roles: namely, as a high-surface-area organic/aqueous phase contactor, as an organic/aqueous phase separator, and as an interfacial biocatalyst. By placing a hydrophilic membrane at the interface between immiscible aqueous and organic process streams in a membrane module characterized by a high membrane area packing density, it is possible to provide a large organic/aqueous and fluid/membrane contact area without the necessity of dispersing one immiscible phase within the other as is more conventional practice.

More specifically, feeding the racemic d,l-trans methyl ester of 3-(4-methoxyphenyl)glycidic ester to a multiphase/extractive membrane reactor in the form of a solution of the substrate in a water-immiscible organic solvent as shown in the process of FIG. 7 is advantageous for several reasons. On the one hand, the multiphase membrane reactor promotes efficient contact of the poorly water-soluble substrate ester with the membrane-contained enzyme, minimizing diffusional resistances associated with the bulk aqueous phase typically present in non-membrane dispersed-phase operation of such reactions. Additionally, this efficient contact of substrate with enzyme minimizes the undesirable non-catalytic side reactions of the substrate, e.g., hydrolysis of the oxirane ring of the glycidate ester to form diol compounds. Such undesirable hydrolytic side reactions of the substrate can reduce the yield of the enzymatic resolution process and should be minimized, as is possible with the multiphase/extractive membrane reactor of the present invention. The multiphase/extractive membrane reactor provides a high concentration of enzyme at the organic/aqueous interface, thereby maximizing the ratio of the rate of the desired enzymatic hydrolysis of the (2S,3R)-glycidate ester to the rate of the undesired non-catalyzed hydrolysis of the oxirane ring of the (2R,3S)-glycidate ester and maximizing yield of the desired (2R,3S)-glycidate ester reaction product in the process.

A further benefit of conducting the enzymatic resolution process in a multiphase/extractive membrane reactor of FIG. 7 relates to the ability to selectively and efficiently remove or "extract" an inhibitory reaction product from the reaction zone without unnecessarily diluting and/or losing the enzyme catalyst. By removing one or more of the water-soluble ester hydrolysis products (i.e., either or both of the alcohol or glycidic acid species including any subsequent decomposition products such as the aldehyde formed from the glycidic acid) from the reactor via the aqueous process stream, the local concentration of inhibitory product in contact with the enzyme can be maintained at an arbitrarily low level (determined by the economics of recovering and-/or disposing of it from the aqueous phase). In essence, the reaction product, formed in the enzyme-activated membrane, is diluted to low concentration by the aqueous process stream flowing past it; thus, the inhibitory product is removed from the reactor, at the same time that the enzyme is kept within the membrane at high concentration. In this manner the reaction may be "pulled" to higher conversions than would otherwise be obtained.

General membrane reactor operating parameters are taught in U.S. Pat. No. 4,800,162 as cited above, and more specific parameters and reaction conditions pertinent to the enzymatic resolution of methyl 3-(4-methoxyphenyl)glycidate esters are given below in Sections 5.2 and 5.4 detailing particular examples of the operation of the process.

A preferred means of reversible enzyme containment is described by Matson in U.S. Pat. No. 4,795,704 and in U.S. patent application Ser. No. 912,595 filed Oct. 1, 1986 and entitled "Method and Apparatus for Catalyst Containment in Multiphase Membrane Reactor System," which are incorporated herein by reference. However, many other means for enzyme immobilization on or within membranes well known in the art may alternately be employed. FIG. 8 shows how enzyme is contained within the asymmetric, microporous, and hydrophilic hollow fiber of a multiphase/extractive membrane reactor; additional detail is provided in examples that follow.

5.2. Examples of Multiphase Enzymatic Resolutions

Several examples of the practice of the invention and elements thereof follow. These examples are meant to illustrate more fully the nature of the present invention without acting as a limitation upon its scope.

5.2.0. Procedures for Examples 1–6

The enzymatic resolution experiments of Examples 1 through 6 described below were conducted in a biphasic system consisting of a dispersion of organic-phase substrate in a continuous aqueous phase. More particularly, a racemic mixture of the trans glycidic ester enantiomers of interest was dissolved in a suitable, water immiscible organic phase, and then contacted with an aqueous phase containing a given enzyme preparation. The entire reaction mixture was agitated or stirred vigorously to provide a large interfacial surface area between the phases, permitting rapid partition of the substrate ester and the acid hydrolysis product between the phases, and permitting the enhancement of the interfacial activity of the enzyme in use, in the event that the particular enzyme displayed such activity. The pH of the aqueous phase was maintained at a level amenable to the enzyme in use by a buffer system.

After an appropriate time, the agitation or stirring was stopped, the organic phase was removed, and the aqueous phase was extracted with more of the same organic solvent or diethyl ether used to form the organic phase. The organic layers were combined, washed with water, dried, and evaporated. The resulting material was then checked for optical activity by polarimetry.

Several simple alkyl esters of the racemic trans-3-(4-methoxyphenyl)glycidic acid were screened as substrates for a variety of enzymes. In particular, the methyl, ethyl, iso-propyl, n-butyl, and iso-butyl esters of racemic trans-3-(4-methoxyphenyl)glycidic acid were synthesized via the Darzen's glycidic ester condensation (Annalen der Chemie, 583 (1953) 110; *Organic Reactions*, Vol. 5, p. 413, John Wiley & Sons, N.Y., p. 413, 1968). Each ester was then assayed for susceptibility to enantiospecific hydrolysis by commercially available enzyme preparations according to the following general procedure.

Ten mmoles of the racemic glycidic ester (e.g., 2.08 g in the case of the methyl ester) were dissolved in 50 mls of organic solvent, either toluene or tert-butyl methyl ether, and placed in a flask with 50 mls of 200 mM sodium phosphate buffer of pH 7.0, plus 100 mgs of the enzyme to be assayed. The flask was tightly closed, and placed on a wrist action shaker for 18 hours at ambient temperature (22° to 25° C.). Agitation was then stopped, ad the contents of the flask poured into a separatory funnel. The organic layer was removed, and the aqueous layer washed with more of the same organic solvent or diethyl ether. The organic layers were combined, back-washed with water, and dried over anhydrous magnesium sulfate. The organic solvent was then removed under reduced pressure, and the amount of remaining material recorded. A sample of this material was then dissolved in ethanol at a concentration of 1 g per 100 mls (i.e., c=1.0), and checked for optical activity on a polarimeter.

The results of this procedure applied to a number of enzyme/ester combinations in two organic solvents are listed in Examples 1 through 6 below. The commercial sources of isolated enzymes and enzyme preparations are listed beside the enzyme name.

5.2.1. Example 1—Stereoselective Hydrolysis of trans-3-(4-Methoxyphenyl)glycidic Acid Methyl Ester in tert-Butyl Methyl Ether Table 1 presents results for the enzymatic hydrolysis of the methyl ester compound dissolved in tert-butyl methyl ether; a total of 20 different enzyme preparations were employed in these experiments. The amount of racemic methyl ester subjected to enzymatic resolution was 2.08 g in these tests. The experimental protocol employed was that described in Section 5.2.0.

5.2.2. Example 2—Stereoselective Hydrolysis of trans-3-(4-Methoxyphenyl)glycidic Acid Methyl Ester in Toluene Table 2 presents results for the enzymatic hydrolysis of the methyl ester compound dissolved in toluene; a total of 25 different enzymes and enzyme preparations were employed in these experiments. The amount of racemic methyl ester subjected to enzymatic resolution was 2.08 g in these tests. The experimental protocol employed was that described in Section 5.2.0.

5.2.3. Example 3—Stereoselective Hydrolysis of trans-3-(4-Methoxyphenyl)glycidic Acid Ethyl Ester in tert-Butyl Methyl Ether Table 3 presents results for the enzymatic hydrolysis of the ethyl ester compound dissolved in tert-butyl methyl ether; three different enzyme preparations were employed in these experiments. The amount of racemic ethyl ester subjected to enzymatic resolution was 2.22 g in these tests, which were conducted according to the procedure described in Section 5.2.0.

5.2.4. Example 4—Stereoselective Hydrolysis of trans-3-(4-Methoxyphenyl)glycidic Acid n-Butyl Ester in tert-Butyl Methyl Ether Table 4 presents results for the enzymatic hydrolysis of the n-butyl ester compound dissolved in tert-butyl methyl ether; three different enzyme preparations were employed in these experiments. The amount of racemic n-butyl ester subjected to enzymatic resolution was 2.50 g in these tests, which were conducted according to the procedure described in Section 5.2.0.

5.2.5. Example 5—Stereoselective Hydrolysis of trans-3-(4-Methoxyphenyl)glycidic Acid Isopropyl Ester in tert-Butyl Methyl Ether Table 5 presents results for the enzymatic hydrolysis of the isopropyl ester compound dissolved in tert-butyl methyl ether; four different enzyme preparations were employed in these experiments. The amount of racemic isopropyl ester subjected to enzymatic resolution was 2.36 g in these tests, which were conducted according to the procedures described in Section 5.2.0.

5.2.6. Example 6—Stereoselective Hydrolysis of trans-3-(4-Methoxyphenyl)glycidic Acid Isobutyl Ester in tert-Butyl Methyl Ether Table 6 presents results for the enzymatic hydrolysis of the isobutyl ester compound dissolved in tert-butyl methyl ether; a single enzyme preparation was employed in this experiment. The amount of racemic isobutyl ester subjected to enzymatic resolution was 2.50 g in this test, which was conducted according to the experimental protocol described in Section 5.2.0.

TABLE 1

Substrate: trans 3-(4-methoxyphenyl)glycidic acid methyl ester
Solvent: tert-butyl methyl ether

| Enzyme | (Enzyme Source) | Recovered Material | $[\alpha]$ (degrees) $c = 1$ in EtOH |
|---|---|---|---|
| Candida Lipase-OF | (Meito Sangyo) | .960 g | −0.360 |
| Lipase AK | (Amano) | .980 g | −0.500 |
| Lipase AP-12 | (Amano) | 1.00 g | −0.200 |
| Lipase D | (Amano) | .900 g | −0.370 |
| Lipase FAP | (Amano) | .900 g | −0.445 |
| Lipase GC-20 | (Amano) | .980 g | −0.031 |
| Lipase P | (Amano) | .980 g | −0.582 |
| Lipase RH | (Tanabe) | 1.24 g | −0.165 |
| Protease HT | (Miles) | .900 g | −0.148 |
| Protease N | (Amano) | 1.00 g | −0.132 |
| Protease 8 | (Sigma) | 1.22 g | −0.255 |
| Protease 16 | (Sigma) | 800 g | −0.708 |
| Protease 24 | (Sigma) | 940 g | −0.600 |
| Protease 27 | (Sigma) | 880 g | −0.698 |
| Alcalase | (Novo) | 1.26 g | −0.365 |
| Maxatase | (Gist-Brocades) | 1.04 g | −0.208 |
| Prozyme 6 | (Amano) | 1.00 g | −0.077 |
| PLE | (Sigma) | .700 g | −0.168 |
| AFP 2000 | (Miles) | 1.04 g | −0.027 |
| Chr.viscosum | (Toyo Jozo) | 1.10 g | −0.131 |

PLE = Pig liver esterase

TABLE 2

Substrate: trans 3-(4-methoxyphenyl)glycidic acid methyl ester
Solvent: toluene

| Enzyme | (Enzyme Source) | Recovered Material | $[\alpha]$ (degrees) $c = 1$ in EtOH |
|---|---|---|---|
| Lipase N | (Amano) | .800 g | −0.386 |
| Lipase Rh.arr. | (Boehringer Mannheim) | .760 g | −0.470 |
| Lipase R-10 | (Amano) | 1.84 g | −0.010 |
| Lipase K-10 | (Amano) | 1.80 g | −0.128 |
| Lipase L | (Amano) | 1.50 g | −0.035 |
| Lipase MAP | (Amano) | 1.37 g | −0.804 |
| PPL | (Sigma) | 1.58 g | −0.017 |
| Wheat germ | (Sigma) | 1.60 g | −0.010 |
| Papain | (Sigma) | 1.84 g | −0.031 |
| Protease 1 | (Sigma) | 1.72 g | 0.0 |
| Protease 10 | (Sigma) | 1.10 g | −0.010 |
| Protease 14 | (Sigma) | 1.91 g | −0.016 |
| Protease 18 | (Sigma) | .940 g | +0.007 |
| Protease 27 | (Sigma) | 1.91 g | −0.241 |
| Protease 2A | (Amano) | 1.84 g | −0.067 |
| Protease HT | (Miles) | 1.47 g | −0.140 |
| Protease FPC | (Miles) | 1.59 g | −0.011 |
| Acylase 1 | (Sigma) | 1.66 g | 0.0 |
| Palatase A | (Novo) | 1.53 g | −0.014 |
| Palatase M | (Novo) | 1.42 g | −0.791 |
| Sumizyme | (Miles) | 1.52 g | −0.033 |
| Thermoase | (Miles) | 1.60 g | −0.006 |
| Mucor miehei | (Biocatalysts) | 1.46 g | −0.762 |
| Mucor javanicus | (Biocatalysts) | 1.28 g | −0.972 |
| H. languinosa | (Biocatalysts) | 1.41 g | −0.357 |
| LPL 200S | (Amano) | 1.12 g | −0.137 |
| Candida Lipase-OF | (Meito Sangyo) | 1.20 g | −1.029 |

PPL = Porcine pancreatic lipase

TABLE 3

Substrate: trans 3-(4-methoxyphenyl)glycidic acid ethyl ester
Solvent: tert-butyl methyl ether

| Enzyme | (Enzyme Source) | Recovered Material | $[\alpha]$ (degrees) $c = 1$ in EtOH |
|---|---|---|---|
| Candida Lipase-OF | (Meito Sangyo) | 1.01 g | −0.416 |
| Alcalase | (Novo) | 1.50 g | −0.375 |

TABLE 3-continued

Substrate: trans 3-(4-methoxyphenyl)glycidic acid ethyl ester
Solvent: tert-butyl methyl ether

| Enzyme | (Enzyme Source) | Recovered Material | [α] (degrees) c = 1 in EtOH |
|---|---|---|---|
| Protease 8 | (Sigma) | 1.45 g | −0.337 |

TABLE 4

Substrate: trans 3-(4-methoxyphenyl)glycidic acid n-butyl ester
Solvent: tert-butyl methyl ether

| Enzyme | (Enzyme Source) | Recovered Material | [α] (degrees) c = 1 in EtOH |
|---|---|---|---|
| Candida Lipase-OF | (Meito Sangyo) | 1.59 g | −0.002 |
| LPL 200S | (Amano) | 1.39 g | −0.004 |
| PLE | (Sigma) | 1.57 g | −0.006 |

LPL = Lipoprotein lipase; PLE = Pig liver esterase

TABLE 5

Substrate: trans 3-(4-methoxyphenyl)glycidic acid isopropyl ester
Solvent: tert-butyl methyl ether

| Enzyme | (Enzyme Source) | Recovered Material | [α] (degrees) c = 1 in EtOH |
|---|---|---|---|
| Candida Lipase-OF | (Meito Sangyo) | 1.33 g | −0.393 |
| Protease 16 | (Sigma) | 1.83 g | −0.065 |
| Protease 24 | (Sigma) | .850 g | −0.044 |
| Protease 27 | (Sigma) | .780 g | −0.064 |

TABLE 6

Substrate: trans 3-(4-methoxyphenyl)glycidic acid iso-butyl ester
Solvent: tert-butyl methyl ether

| Enzyme | (Enzyme Source) | Recovered Material | [α] (degrees) c = 1 in EtOH |
|---|---|---|---|
| Candida Lipase-OF | (Meito Sangyo) | 1.01 g | −0.521 |

Particularly preferred enzymes for the stereoselective hydrolysis of the (2S,3R) enantiomer of methyl 3-(4-methoxyphenyl)glycidate include the lipase designated "Lipase MAP" available from Amano, the lipase designated "Candida Lipase-OF" available from Meito Sangyo, and the protease designated "Protease 27" available from Sigma Chemical Co. These enzymes are attractive for the reasons that they possess good activity towards the simple methyl ester substrate. Additionally, these two enzymes exhibit particularly good stereoselectivity for hydrolysis of the (2S,3R)-glycidate ester in preference to its (2R,3S) counterpart. Both Lipase MAP and Protease 27 leave predominantly negatively rotating species in the organic phase upon completion of the enzymatic reaction, signifying enrichment of the relatively unreactive and negatively rotating (2R,3S)-glycidate ester in the organic phase. The relatively high stereoselectivity of the Protease 27, Lipase MAP, and Lipase-OF enzymes toward the methyl ester compound is evidenced by the relatively large magnitude of the optical rotations reported in Tables 1 and 2, respectively.

The data summarized in Tables 1 through 6 demonstrate that all of the five simple straight- and branched-chain alkyl esters investigated did, in fact, exhibit at least some degree of susceptibility to enzymatic hydrolysis. However, reaction rates and optical rotations obtained with the several substrate/enzyme combinations studied were found to vary considerably. For example, experiments with the n-butyl ester (see Table 4) yielded products with very small optical rotations, indicative of little or no enzyme action and/or stereoselectivity, whereas experiments with the methyl ester gave optical rotations as high as about −0.8° for several enzymes (Table 2). The methyl ester of 3-(4-methoxyphenyl)glycidate is a particularly preferred substrate ester, because methanol is inexpensive and readily available. Additionally, existing commercial processes for the manufacture of diltiazem utilize the methyl glycidate ester directly as an intermediate, as opposed to using other alkyl and aryl glycidate esters. For this reason, production and use of the resolved methyl glycidate ester intermediate in a diltiazem manufacturing process results in a simpler and more economical process than would be obtained with other resolved glycidate ester precursors.

5.2.7. Effect of Cosolvent on Apparent Enantioselectivity E: Example 7

An additional aspect of the present invention pertains to the enhancement of enzyme enantioselectivity by the addition of small amounts of organic co-solvents to the aqueous phase, and by the judicious choice of the organic solvent used as the water-immiscible phase.

It is generally known that water-miscible organic solvents can have a significant although unpredictable effect on the enantioselectivity of enzymes. In the case of one of the commercial enzyme preparations, the presence of methanol as 5% of the aqueous phase dramatically increased the apparent E value. The procedure followed to investigate this effect is described below, and the results tabulated.

In Example 7, 100 mgs of Lipase MAP from Amano were added to each of two flasks, each containing 10 mmoles of racemic trans 3-(4-methoxyphenyl)glycidic acid methyl ester that had been dissolved in 50 mls of toluene, plus an aqueous phase of 0.2M sodium phosphate buffer of pH 7.0 In one flask, the aqueous phase consisted entirely of buffer (50 mls), while in the other flask the aqueous phase was composed of 47.5 mls of buffer plus 2.5 mls of methanol. Each flask was agitated at ambient temperature for 18 hours, and the organic phase was subsequently separated, dried and evaporated to leave a solid material. This solid material was weighed and the degree of hydrolysis "x" was calculated. The optical rotation was measured in ethanol at a concentration of c=1 (i.e., [α]), and the enantiomeric excess of the remaining glycidic ester was calculated (i.e., ee(S)). These results are summarized in Table 7.

TABLE 7

Effect of Methanol on Apparent Enantioselectivity E

| | x | [α] | ee(S) | E |
|---|---|---|---|---|
| 0% MeOH | .35 | −0.804° | 41% | 11 |
| 5% MeOH | .20 | −0.811° | 41% | >200 |

5.2.8. Effect of Water-Immiscible Organic Solvent on Apparent Enantioselectivity E: Example 8

The choice of the water-immiscible organic solvent for the racemic ester substrate represents yet another reaction variable. Using E values as a basis of comparison, the effect of the water-immiscible solvent on the apparent enantioselectivity of a given enzyme may be quantified. The procedure followed to investigate this effect is outlined below.

In Example 8, 100 mgs of enzyme preparation were dissolved or dispersed in 50 mls of 0.2M sodium phosphate buffer of pH 7.0 To this were added 50 mls of water-immiscible organic solvent in which 10 mmoles of racemic trans-3-(4-methoxyphenyl)glycidic acid methyl ester had been dissolved. The reaction flask was capped, and agitated at ambient temperature for 18 hours. The organic layer was then separated, dried, and evaporated in order to recover the non-hydrolyzed glycidic ester. This remaining material was weighed to determine the degree of overall hydrolysis, and its optical rotation was measured in ethanol to determine its enantiomeric excess. The apparent E values calculated for various enzymes in the presence of three different water-immiscible organic phases are summarized in Table 8.

5.2.9. Effect of pH on Enzyme Enantioselectivity E: Example 9

Another factor important to enzyme behavior is the pH of its aqueous environment. It is well known that the activity of enzymes can be strongly pH-dependent, with enhanced catalytic activity in certain pH ranges and lessened activity outside of that range. Less well recognized and more poorly understood is the fact that enzymes may also exhibit pH optima with respect to enantioselectivity as well as activity, particularly since enzyme selectivity is generally thought to arise from steric effects. To investigate this effect with respect to the resolution of racemic trans-3-(4-methoxyphenyl)glycidic acid methyl ester, the aqueous phase in the reaction system was adjusted to varying pH values. The procedure employed is described below.

10 mmoles of the racemic trans-3-(4-methoxyphenyl)glycidic acid methyl ester were dissolved in 50 ml of toluene and placed in a flask with 50 ml of 200 mM sodium phosphate buffer of varying pH values, along with 100 mg of Lipase MAP obtained from Amano. The flask was tightly closed and placed on a wrist-action shaker for 18 hours at ambient temperature. Agitation was then stopped, and the reaction mixture was worked up as described above. Results are summarized in Table 9, which indicates an optimum pH with respect to enzyme enantioselectivity of about 8.0.

TABLE 8

| Effect of Organic Solvent on Apparent Enantioselectivity E | | | |
|---|---|---|---|
| | Organic Solvent: | | |
| | tBME | Toluene | Chloroform |
| Enzyme: | | | |
| Lipase MAP | N/D | 11.4 | 2.5 |
| Lipase P | 2.4 | 2.7 | N/D |
| Protease 16 | 2.2 | 3.2 | N/D |
| Protease 27 | 2.5 | 9.7 | 2.3 |

N/D = Not determined

TABLE 9

| Effect of pH on Enantioselectivity | | |
|---|---|---|
| pH of Aqueous Phase | Recovered Material | Rotation [α] (c = 1 in ethanol) |
| 6.0 | 1.10 g | −0.593° |
| 6.5 | 1.40 g | −0.685° |
| 7.0 | 1.40 g | −0.870° |
| 7.5 | 1.50 g | −0.893° |
| 8.0 | 1.60 g | −0.926° |

TABLE 9-continued

| Effect of pH on Enantioselectivity | | |
|---|---|---|
| pH of Aqueous Phase | Recovered Material | Rotation [α] (c = 1 in ethanol) |
| 8.5 | 1.78 g | −0.780° |

Thus, preferred embodiments of this invention include the use of an aqueous phase containing 5% methanol by volume (and, obviously, other concentrations), the use of toluene as the water-immiscible organic solvent, and conduct of the reaction with an aqueous-phase pH of about 8.

5.2.10. Methyl Ester Hydrolysis Catalyzed by Lipase MAP—Examples 10 and 11

Additional experimental examples were carried out with the preferred substrate (i.e., the methyl ester) and one of the preferred enzymes (i.e., Amano's Lipase MAP) in order to further explore the effect of various reaction parameters and to better understand their influence on the resolution process efficiency.

Example 10. A hydrolysis experiment was carried out in the following manner. An enzyme solution was prepared by dissolving 276 mg of Lipase MAP (Amano) in 50 ml of 0.01M sodium phosphate buffer, pH 7.00. A substrate solution containing 2.23 g (10.74 mmoles) of racemic methyl 3-(4-methoxyphenyl)glycidate (MMPG) and 25 ml of toluene was added to the enzyme solution. The pH was controlled in a "pH stat" at 7.00 by the addition of a sodium hydroxide solution (1 mole/L). The addition of NaOH ceased after a total of 0.97 ml of base had been added, corresponding to a conversion of ester to acid of 9.03% (i.e., 100*0.97/10.74). To test whether loss of enzymatic activity was the reason for the reaction's stopping at this point, an additional 127 mg of enzyme were added. No consumption of base was observed after adding the enzyme. The effect of the presence of reaction product on the degree of conversion was tested by introducing an additional 50 ml of water to the reaction mixture to dilute the concentration of reaction products. Immediately after doing so, base consumption began and stopped after the total volume of NaOH added was 1.31 ml. The calculated conversion corresponding to this total acid generation/base consumption was 12.2% (i.e., 100*1.31/10.74).

Example 11. An additional hydrolysis experiment was carried out in the following manner. An enzyme solution was prepared by dissolving 537 mg of Lipase MAP (Amano) in 1000 ml of 0.01M sodium phosphate buffer pH 7.00. A substrate solution containing 2.18 g (10.51 mmoles) of racemic methyl 3-(4-methoxyphenyl)-glycidate (MMPG) and 25 ml of toluene was added to the enzyme solution. The pH was controlled in a "pH stat" at 7.00 by the addition of a sodium hydroxide solution (1 mole/L). The addition of NaOH ceased after a total of 3.38 ml of base had been added, corresponding to an ester conversion of 32.16% (i.e., 100*3.38/10.51). To test whether loss of enzymatic activity was the reason for the reaction's stopping at this point, an additional 490 mg of enzyme were added. No additional base consumption was observed after adding the enzyme. The effect of product species concentration on the degree of conversion was tested by introducing an additional 2.25 g of MMPG (10.81 mmoles) in 25 ml of toluene to the reaction mixture. Immediately after doing so, base consumption began and stopped after the total volume of NaOH added was 5.71 ml. The final conversion at this point was 26.78% (i.e., 100*5.71/(10.51+10.81)).

An effective "pseudo-equilibrium" concept is used herein to describe the reaction process, particularly the inhibitory effect of species concentrations on the "equilibrium" conversion. Because the enzymatic hydrolysis reaction was observed to stop once a certain concentration of inhibitory product had accumulated in the system, the reaction process can be described as if the reaction were a thermodynamically "reversible" one, without wishing to be limited as to the specific mechanism of inhibition of the reaction by reaction products or by-products. That is, the reaction can be considered to proceed to a certain "equilibrium" conversion which is dependent on the concentration of inhibitory product or by-product.

5.2.11. Methyl Ester Hydrolysis Catalyzed by Lipase-OF—Example 12

An additional hydrolysis experiment with Lipase-OF enzyme was carried out in the following manner. An enzyme solution was prepared by dissolving 64 mg of Lipase-OF (derived from Candida cylindracea, supplied by Meito Sangyo Co.) in 100 ml of 0.05M sodium phosphate buffer pH 8.00. A substrate solution containing 2.6 g (12.5 mmoles) of racemic methyl 3-(4-methoxyphenyl)glycidate (MMPG) and 25 ml of toluene was added to the enzyme solution. The pH was controlled in a "pH stat" at 8.00 by the addition of a sodium hydroxide solution (0.1 mole/L). After a total of 46.3 ml of base had been added (corresponding to 40% hydrolysis of the ester), the remaining ester was isolated in the manner described above. The enantiomeric excess of the isolated ester product was 87.3% as determined by HPLC. The amount of ester recovered was 1.34 g corresponding to a 52% yield.

5.2.12. Resolution of Racemic Methyl 3-(4-Methoxyphenyl)glycidate in a Membrane Reactor at pH 7—Example 13

A multiphase/extractive membrane reactor for this equilibrium-limited enzymatic resolution process could be operated at pH 7.0 in the following manner. The enzyme could be immobilized in the membrane by any one of the conventional methods reported in the literature pertaining to the type of membrane being used. In a preferred embodiment, the enzyme would be immobilized by its reversible containment inside an asymmetric, hydrophilic, microporous hollow-fiber membrane as described by Matson in U.S. Pat. No. 4,795,704 and in copending U.S. patent application Ser. No. 912,595. More particularly, the multiphase/extractive membrane reactor used in this resolution process could consist of a 0.75 m2 custom-made solvent-resistant membrane module fabricated with polyacrylonitrile hollow fibers of the type used in hemofiltration applications and available, for example, from Asahi Co. The enzyme, Lipase MAP, purchased from Amano International Enzymes, has been shown to have an activity of 6 $\mu$moles of MMPG hydrolyzed per hour per mg of enzyme preparation. This enzyme has also been shown to stereoselectively hydrolyze simple alkyl esters of 3-(4-methoxyphenyl)glycidic acid.

To activate the membrane module with enzyme, 5.0 grams of the enzyme could be dissolved in 1 liter of distilled water. The enzyme solution would then be recirculated in an ultrafiltration mode from the shell into lumen and back to the reservoir for 30 minutes. The ultrafiltrate would be collected until the reservoir is empty, and 250 ml of toluene would subsequently be pumped into the shell and recirculated at 400-450 ml/min with a 5-7 psig shell pressure to remove any remaining enzyme solution from the shell-side space in the reactor module.

After loading the enzyme into the reactor, 100 L of 10 mM phosphate buffer pH 7.00 previously saturated with toluene would be recirculated on the lumen side at a flow rate of 400-500 ml/min. This large volume of aqueous buffer would be required in order to overcome the "reversibility" of the partitioning/reaction process at pH 7, as discussed above. By providing a large aqueous volume, inhibitory products can be diluted to low aqueous-phase concentrations, and the reaction "equilibrium" can thus be displaced to acceptably high conversions. Next, 20.8 g (0.1 mole) of racemic methyl 3-(4-methoxyphenyl)glycidate (MMPG) would be added to the toluene reservoir. The pH of the aqueous reservoir would be kept at 7.00 by the addition of 1.0M NaOH. The reactor would be run continuously until the degree of ester hydrolysis approached 65%, i.e., until 65 ml of 1M NaOH had been added. At this point the organic phase would be drained from the membrane reactor, and the remaining MMPG would be isolated from the organic phase in the manner described above.

Feeding the racemic d,l-trans methyl ester of 3-(4-methoxyphenyl)glycidic ester to a multiphase/extractive membrane reactor in the form of a solution of the substrate in a water-immiscible organic solvent is advantageous for several reasons. On the one hand, the multiphase membrane reactor promotes efficient contact of the poorly water-soluble substrate ester with the membrane-contained enzyme, minimizing diffusional resistances associated with the bulk aqueous phase typically present in non-membrane dispersed-phase operation of such reactions. On the other hand, this efficient contact of substrate with enzyme also minimizes the undesirable non-catalytic side reactions of the substrate, e.g., hydrolysis of the oxirane ring of the glycidate ester to form diol compounds. Such undesirable hydrolytic side reactions of the substrate can reduce the yield of the enzymatic resolution process and should be minimized, as is possible with the multiphase/extractive membrane reactor of the present invention. The multiphase/extractive membrane reactor provides a high concentration of enzyme at the organic/aqueous interface, thereby maximizing the ratio of the rate of the desired enzymatic hydrolysis of the (2S,3R)-glycidate ester to the rate of the undesired non-catalyzed hydrolysis of the oxirane ring of the (2R,3S)-glycidate ester and maximizing yield of the desired (2R,3S)-glycidate ester reaction product in the process.

An additional benefit of conducting the enzymatic resolution process in a multiphase/extractive membrane reactor relates to the ability to selectively and efficiently remove inhibitory reaction product from the reaction zone without unnecessarily diluting and/or losing the enzyme catalyst. One the one hand, this may be accomplished by removing a water-soluble inhibitory product via dilution in the aqueous process stream or by chemical reaction therein (e.g., bisulfite adduct formation as discussed in Sections 5.3 and 5.4). Alternatively, inhibitory reaction products that exhibit significant solubility in organic solvents can be removed from the reaction system by extracting them from the organic phase, either in conventional liquid-liquid contacting equipment or in membrane solvent extraction equipment. Certain inhibitory products (e.g., the aldehyde reaction by-product discussed in Sections 5.3 and 5.4) are soluble to a certain degree in both aqueous and organic solutions, and thus are amenable to being managed by either approach.

5.2.13. Resolution of Racemic Methyl 3-(4-Methoxyphenyl)glycidate in a Membrane Reactor at pH 8 Examples 14-17

Four membrane reactor resolution experiments (corresponding to Examples 4-17) were conducted at pH 8 (as opposed to the pH value of 7 employed in Example 13).

Example 14. A multiphase membrane reactor for this resolution process was operated in the following manner. The membrane reactor consisted of a 0.75 m$^2$ solvent resistant membrane module fabricated with polyacrylonitrile ultrafiltration hollow fibers. The enzyme Lipase MAP, purchased from Amano International Enzymes, has been shown to have an activity of 6 $\mu$moles of MMPG hydrolyzed per hour per mg. This enzyme has also been shown to stereo-selectively hydrolyze esters of 3-(4-methoxyphenyl)glycidic acid.

The membrane reactor was loaded with enzyme in the manner described in Sections 6.6 and 6.7. Specifically, 5.0 grams of the enzyme were dissolved in 1 liter of distilled water. The enzyme solution was then recirculated in an ultrafiltration mode with fluid flowing from the shell into the lumen and back to the reservoir for 30 minutes. The ultrafiltrate was then collected until the reservoir was empty, and 250 ml of toluene were subsequently pumped into the shell and recirculated at 400-450 ml/min with a 5-7 psig shell pressure to remove any remaining enzyme solution from the shell.

After thus loading enzyme into the reactor, 1 L of 0.2M phosphate buffer at pH 8.00 were recirculated on the lumen side at a rate of 400-500 ml/min. To start the run, 20.8 g (0.1 mole) of methyl 3-(4-methoxyphenyl) glycidate (MMPG) were added to the toluene reservoir. The pH of the aqueous reservoir was kept at 8.00 by addition of 0.9M NaOH. The reactor ran continuously until the degree of ester hydrolysis reached 57.5% based on the amount of caustic consumed. At this point the organic phase was drained and the remaining MMPG was isolated. The enantiomeric excess of the isolated ester product was 96% as determined by polarimetry. The amount of ester recovered was 4 g, corresponding to a 19% yield.

Example 15. The multiphase membrane reactor described in Example 14 was reused in the following experiment. 375 ml of toluene were pumped into the shell and recirculated at 400-450 ml/min with a 5-7 psig shell pressure to remove any remaining enzyme solution from the shell. An aqueous volume of 1.5 L of 0.2M phosphate buffer pH 8.00 was recirculated on the lumen side at a rate of 400-500 ml/min. To start the run, 31.2 g (0.15 mole) of methyl 3-(4-methoxyphenyl) glycidate (MMPG) were added to the toluene reservoir. The pH of the aqueous reservoir was kept at 8.00 by the addition of 0.9M NaOH. The reactor ran continuously until the degree of ester hydrolysis reached 53% based on the amount of caustic consumed. At this point the organic phase was drained and the remaining MMPG was isolated. The enantiomeric excess of the isolated ester product was 99% as determined by polarimetry. The amount of ester recovered was 5.9 g, corresponding to a yield of 19%.

Example 16. The multiphase membrane reactor described in Example 14 was reused in the following experiment. 375 ml of toluene were pumped into the shell and recirculated at 400-450 ml/min with a 5-7 psig shell pressure to remove any remaining enzyme solution from the shell. An aqueous volume of 1.5 L of 0.2M phosphate buffer pH 8.00 was recirculated on the lumen side at a rate of 400-500 ml/min. To start the run, 31.2 g (0.15 mole) of methyl 3-(4-methoxyphenyl) glycidate (MMPG) were added to the toluene reservoir. The pH of the aqueous reservoir was kept at 8.00 by the addition of 0.9M NaOH. The reactor ran continuously until the degree of ester hydrolysis reached 52.4% based on the amount of caustic consumed. At this point the organic phase was drained and the remaining MMPG was isolated. The enantiomeric excess of the isolated ester product was 99% as determined by polarimetry. The amount of ester recovered was 9.0 g, corresponding to a yield of 28.8%.

Example 17. The multiphase membrane reactor described in Example 14 was reused in the following experiment. 375 ml of toluene were pumped into the shell and recirculated at 400-450 ml/min with a 5-7 psig shell pressure to remove any remaining enzyme solution from the shell. An aqueous volume of 1.5 L of 0.2M phosphate buffer pH 8.00 was recirculated on the lumen side at a rate of 400-500 ml/min. To start the run, 31.2 g (0.15 mole) of methyl 3-(4-methoxyphenyl) glycidate (MMPG) were added to the toluene reservoir. The pH of the aqueous reservoir was kept at 8.00 by the addition of 0.9M NaOH. The reactor ran continuously until the degree of ester hydrolysis reached 41.2% based on the amount of caustic consumed. At this point the organic phase was drained and the remaining MMPG was isolate. The enantiomeric excess of the isolated ester product was 92% as determined by polarimetry. The amount of ester recovered was 7.7 g, corresponding to a yield of 24.8%.

5.3. Management of the Aldehyde Byproduct by Adduct Formation with Bisulfite A preferred method for resolving a racemic mixture of a trans-glycidic acid ester compound of the formula I

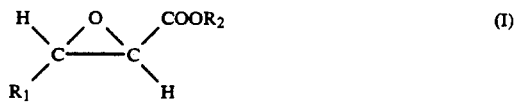

wherein R$_1$ is selected from the group of phenyl or substituted phenyl and R$_2$ is a group derived from an alcohol comprises the steps of a. preparing an organic solution of a racemic compound of formula I containing a first and a second stereoisomer by dissolving said racemic compound in a water-immiscible organic solvent;

b. contacting said organic solution of first and second stereoisomers with an aqueous mixture comprising water, an enzyme, and bisulfite anion, wherein said enzyme stereoselectively catalyzes hydrolysis of the first stereoisomer to form an alcohol compound of the formula R$_2$OH and a corresponding trans-glycidic acid compound of formula II

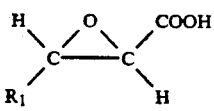
(II)

said acid subsequently reacting spontaneously by decarboxylation and rearrangement to form an aldehyde by-product of the formula III

 (III)

wherein said aldehyde of formula III reacts with said bisulfite anion to form a water-soluble adduct of the formula IV

 (IV)

and;

c. isolating from said organic solution a resolved preparation of said second stereoisomer of formula I.

An additional method for resolving a racemic mixture of a trans-glycidic acid ester compound of the formula I

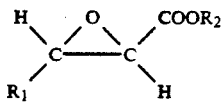 (I)

wherein $R_1$ is selected from the group of phenyl or substituted phenyl and $R_2$ is a group derived from an alcohol, the method comprising:

a. providing an organic solution comprising a water-immiscible organic solvent and a racemic compound of formula I containing a first and a second stereoisomer to a first side of a membrane; and b. providing to a second side of a membrane an aqueous mixture comprising water, an enzyme, and bisulfite anion, wherein said enzyme stereo-selectively catalyzes hydrolysis of said first stereoisomer to form an alcohol compound of the formula $R_2OH$ and a corresponding trans-glycidic acid compound of formula II

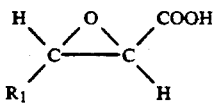 (II)

said acid subsequently reacting spontaneously by decarboxylation and rearrangement to form an aldehyde by-product of the formula III

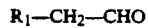 (III)

wherein said aldehyde of formula III reacts with said bisulfite anion to form a water-soluble adduct of the formula IV

 (IV)

whereby said racemic compound of said organic solution is resolved, with said second stereoisomer of formula I principally remaining in said organic solution.

Yet another preferred method for resolving a racemic mixture of a trans-glycidic acid ester compound of the formula I comprises the steps of

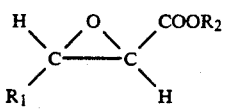 (I)

wherein $R_1$ is selected from the group of phenyl or substituted phenyl and $R_2$ is a group derived from an alcohol, the method comprising:

a. providing an organic solution comprising a water-immiscible organic solvent and a racemic compound of formula I containing a first and a second stereoisomer to one side of an enzyme-activated membrane, wherein said enzyme which activates said membrane catalyzes the hydrolysis of said first stereoisomer to form an alcohol compound of the formula $R_2OH$ and a corresponding trans-glycidic acid compound of formula II

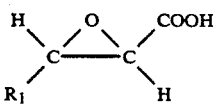 (II)

said acid subsequently reacting spontaneously by decarboxylation and rearrangement to form an aldehyde by-product of the formula III

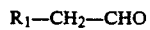 (III)

and b. providing concurrently an aqueous solution containing bisulfite anion, said aqueous solution being substantially immiscible with said organic solution, to the opposite side of said enzyme-activated membrane, wherein said aldehyde of formula III reacts with said bisulfite anion to form a water-soluble adduct of the formula IV

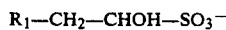 (IV)

whereby said racemic compound of said organic solution is resolved, with said second stereoisomer of formula I principally remaining in said organic solution.

The enzyme-catalyzed hydrolysis of the ester function of the substrate compound A of FIG. 9—trans-3-(4-methoxyphenyl glycidic acid methyl ester—can be observed by titration of the enzymatic reaction mixture with caustic and by following depletion of the substrate by HPLC methods. However, the corresponding glycidic acid, compound B of FIG. 9, cannot be isolated in significant quantities during work-up of the reaction mixture. In the case of enzymatic reactions allowed to run to relatively high conversion of the reactive substrate enantiomer, removal of the organic solvent from the organic phase reaction product mixture left products in addition to the desired products, the (2R,3S) enantiomer of compound A. The presence of such additional products both reduced the purity of the desired product and made more difficult the recovery of the desired product.

Glycidic acids such as compound B, shown in FIG. 9, are generally known to undergo facile decarboxylation and subsequent rearrangement to the corresponding aldehyde. A two-step mechanism for this reaction has been proposed [Singh and Kagan, J. Org. Chem., (1970), 53, 2203]. The resulting compound C, 4-methoxyphenylacetaldehyde, may also be expected to undergo some degree of aerial oxidation by atmospheric oxygen, to give the corresponding carboxylic acid compound D, 4-methoxyphenylacetic acid.

Spectroscopic analysis of the material recovered from the organic phase remaining after the enzyme-catalyzed hydrolysis of compound A, and after removal of the remaining desired (2R,3S) enantiomer of compound A, indicated the presence of both 4-methoxyphenylacetaldehyde, and 4-methoxyphenylacetic acid—that is, compounds C and D, respectively.

Compounds C and D can only be formed from compound A through hydrolysis, whether enzyme- or base-catalyzed, of the methyl ester function of compound A. Furthermore, the aldehyde compound C may react further. Such further reaction may include not only the specific example of oxidation to the corresponding carboxylic acid compound D, experimentally observed by spectroscopic methods, but also adduct formation reactions, hydration to the gem-diol, oligomerization (such as the formation of the trimeric compound analogous to that formed by formaldehyde), and aldol condensation, under either acidic or basic conditions, leading to a large number of possible oligomeric or polymeric products. Additionally, aldehydes can participate in Schiff-base formation, a well-known chemical reaction [J. March, *Advanced Organic Chemistry*, McGraw-Hill Co., 2nd Ed. 1977; Hendrickson, Cramm, and Hammond, *Organic Chemistry*, McGraw-Hill Co., 3rd Ed. 1970]. Generally, most Schiff-bases are stable near neutral pH, and hydrolyze under either acid or base conditions. However, the mechanism of formation involves nucleophilic attack of a non-protonated amine nitrogen on the carbonyl compound in question, such as an aldehyde, and thus Schiff-base formation proceeds more rapidly at pH conditions above pH 7.

As it relates to enzyme reactions, the presence in the reaction system of the aldehyde compound C is cause for concern, inasmuch as Schiff-base formation between aldehydes and the ε-amino groups of lysine residues is well known [T. E. Creighton, *Proteins: Structures and Molecular Properties*, Freeman and Co., 1983]. The resulting modification of an enzyme may give rise to both reversible and irreversible deleterious effects on an enzyme's ability to catalyze a given reaction.

As used herein, the terms "inhibition" and "inhibitory" are meant to describe any process or phenomenon whereby a chemical compound—more particularly a reaction product or byproduct—causes a decrease in the ability of an enzyme to catalyze a given reaction. For example, such inhibition may include that described by the well-known Michaelis-Menten model of enzyme kinetics. This inhibitory effect of a compound on the enzyme may be evident either while the inhibitory compound is in contact with the enzyme during the reaction, or the inhibitory effect may persist after said inhibitory compound has been in contact with the enzyme and subsequently removed. For example, such inhibitory properties may include those associated with compounds which chemically modify the functional groups of amino acid residues of the enzyme protein. Thus, alleviation of both reversible and irreversible forms of inhibition are contemplated in the practice of the present invention.

Inhibitory effects leading to a shortened enzyme life under a given set of reaction conditions will require that the enzyme be replaced more frequently than an enzyme which has a longer lifetime. Taking the average rate of reaction as a measure of enzymatic activity, Table 10 clearly shows that the commercial enzyme preparation Lipase OF operating under the reaction conditions described in Examples 18 and 19 maintains its activity over longer periods of time when the aldehyde byproduct is removed by the addition of bisulfite.

The presence of the aldehyde by-product has important consequences in the operation of a membrane bioreactor used for the resolution of esters of 3-(4-methoxyphenyl) glycidate. In two resolutions done under the reactor conditions described in Example 18, the aqueous phase turned into a white suspension after 15% of the charged ester was titrated. Filtering aliquats of this white suspension through an ultrafiltration membrane removed the white precipitate. However, upon standing for 1 hour, a white suspension appeared in the clear filtrate once again. The demonstrated retention of the precipitate by ultrafiltration suggests that a membrane could be fouled both internally and externally by this material. In experiments done under conditions identical to those in Example 18, but without activating the membrane with enzyme, no white suspension was observed even after 24 hours. Without wishing to be bound to any particular mechanism or explanation, the formation of the white precipitate is consistent with the aldehyde by-product, having a limited but finite water-solubility, being transformed into a water-insoluble product.

In other experiments conducted under the conditions described in Example 18, a solid precipitate was observed present in the aqueous phase. This solid is capable of fouling the inside surface of the membrane and thus reducing its enzymatic activity. In one experiment conducted under the conditions described in Example 18, reversing the aqueous phase flow direction through the fiber lumen resulted in a sudden appearance of yellow particles in the aqueous stream and also a sudden increase in enzymatic activity (as evidenced by an increase in acid titration rate).

The presence of the aldehyde by-product (compound C) also has important implications with regards to the isolation procedure of the final product. As the aldehyde is appreciably organic soluble, it may interfere in the recovery process of the desired product, the (2R,3S) enantiomer of compound A. Increasing amounts of the aldehyde (compound C) in the final organic phase of the reaction mixture make a complete separation of the final product from the aldehyde impurity more difficult and less economical.

For the specific case of enzymatic resolution of glycidate esters, the existence of an aldehyde by-product, compound C, in the reaction mixture suggests a purification method for improving the quality of the final, desired product of the enzyme reaction. This method involves the selective removal of the aldehyde compound C from the organic phase of the enzyme reaction mixture through the selective formation of a bisulfite adduct. This adduct is formed by contacting the organic phase of the enzyme reaction mixture with an aqueous solution of a bisulfite salt, and subsequently extracting the bisulfite adduct into the aqueous phase.

The addition of bisulfite to aldehydes compounds is well known, and mentioned in most organic chemistry textbooks. In general, the carbonyl group of most aldehydes, and some ketones, undergoes nucleophilic attack by the bisulfite anion, leading to the α-hydroxy sulfonate compound E as shown in FIG. 9. Such a compound is generally known as a bisulfite adduct. The stability and ease of formation of such adducts is believed to be determined by the chemical properties of the carbonyl group undergoing the nucleophilic attack. Steric effects are believed to determine the ease of formation of such adducts, and they are generally formed under slightly acidic conditions [Fieser and Fieser, *Reagents for Organic Synthesis, Vol.* 1, John Wiley, 1967], near pH 5, where the nucleophilic $HSO_3^-$ anion is the predominant species in aqueous solution, and the carbonyl group may be slightly protonated, enhancing nucleophilic attack. However, the optimal conditions for both the formation and stability of such adducts are generally considered empirical, and bisulfite adducts are also known to be formed under mildly basic conditions.

Accordingly, a bisulfite solution can be used to wash the organic phase of a dispersed-phase enzymatic reaction after the desired degree of ester hydrolysis is reached, and prior to the removal of the organic solvent comprising the bulk organic phase for the recovery of compound A enriched in the desired (2R,3S) enantiomer. This approach to removing contaminating aldehyde from the desired glycidate ester product is described in Example 20.

However, it was found that a 10% bisulfite solution would also degrade compound A, in the absence of any other hydrolysis reaction products, possibly through attack on the epoxide function by the bisulfite anion, thus leading to a loss of both enantiomers of compound A during reaction work-up. This problem is illustrated in Example 21. This example suggests the existence of an upper limit of bisulfite concentration in a reaction process which cannot exceeded without compromising final product yield.

Example 22 illustrates the decrease in rate of enzyme catalyzed hydrolysis of compound A in the presence of compound C, and the comparative lack of such an inhibitory effect in the presence of compound D. It should be noted that the apparent enhancement by compound D of the rate of hydrolysis by Lipase OF shown in this example is reproducible, and indicates that compound D does not have an inhibitory effect. In addition, the bisulfite adduct, compound E, is not inhibitory, indicating that the stability of the bisulfite adduct under these conditions is sufficient to prevent compound C from exerting its inhibitory effects.

In light of the above information and examples, the possibility exists of removing the inhibitory compound C in situ by formation of its bisulfite adduct during enzymatic hydrolysis of the ester function of compound A. Several factors must be considered in choosing reaction conditions so that the stability of the substrate (compound A), the desired enzymatic activity and enzyme stability, and the ease of formation and stability of the bisulfite adduct of compound C are all maximized. Such work is necessarily empirical, although some information does exist in the open literature. That is, ester functions are generally known to be most stable at close to neutral pH, while epoxides are generally most stable in aqueous solutions between pH 8 and 9.5 [Y. Pocker, B. P. Ronald, and K. W. Anderson, J. Amer. Chem. Soc., (1988), 110, 6492]. Aldehyde-bisulfite adducts are generally known to be stable between pH 5 to 9.

The experimental results shown in Table 11 indicate that the bisulfite adduct, compound E, is sufficiently stable at pH 8 to alleviate the inhibitory effects of compound C. As regards choosing an appropriate bisulfite concentration, the results from Example 21 suggest that 10% w/v is an upper bound if product yield is not to be compromised. At the other extreme, the absence of bisulfite allows the inhibitory effect of compound C to be expressed. Since the stoichiometry of the aldehyde-bisulfite chemistry is one-to-one, a preferred amount of bisulfite anion to be used in the aqueous phase would be an amount equimolar with the amount of aldehyde by-product expected to be generated during the reaction, provided that the volume of aqueous phase is such that the bisulfite concentration does not exceed the upper bound mentioned above.

It should be noted that the bisulfite anion, which exists in aqueous solutions near neutral pH, may be formed by the removal of one proton from sulfurous acid, that is $H_2SO_3$—which itself may be formed through the dissolution and hydration of sulfur dioxide in water. Sulfurous acid may form salts with alkali metals as the corresponding cationic species (e.g., $Na^+$). The anionic species of such salts include bisulfite ($HSO_3^-$), sulfite ($SO_3^{-2}$), and metabisulfite ($S_2O_5^{-2}$). It should further be noted that in an aqueous solution, a mixture of all such forms of sulfurous acid and its salts will exist is an equilibrium mixture, the composition of which will depend on the pH of the solution. An equilibrium between solvated bisulfite anion and sulfite dianion will exist in an aqueous solution over the pH range of 5 to 9, the $pK_a$ of the bisulfite anion being approximately 7. In addition to this equilibrium, one molecule of metabisulfite salt may become hydrated and disproportionate in water to yield two molecules of bisulfite salt. All salts may dissolve to varying degrees to yield the solvated alkali metal cationic species together with solvated bisulfite, sulfite, and metabisulfite anionic species, all of which may subsequently participate in the formation of an equilibrium mixture. In view of the complex equilibria in which the bisulfite anion may participate, the terms "bisulfite concentration" and "bisulfite anion concentration" as used herein are meant to refer to the total concentration of an equilibrium mixture of sulfite, bisulfite, and metabisulfite species—that is, all salts and solvated species, including all the various protonated and ionized species which may be derived from sulfurous acid in aqueous solution—as opposed to referring only to the concentration of the individual anionic bisulfite species $HSO_3^-$ by itself. As all of the above-mentioned species may ultimately be derived from sulfur dioxide, the concentration of bisulfite in an aqueous solution may also be described in terms of the solution's "sulfur dioxide content."

The ratio of organic to aqueous phase volumes is not critical and may be set at any convenient value, consistent with providing in a preferred embodiment at least one equivalent of bisulfite (in the aqueous phase) per mole of compound A (the latter being supplied in the organic phase) to be hydrolyzed in the reaction, and consistent with the concentration of bisulfite in the aqueous phase not exceeding that which causes substrate degradation—e.g., about 10% w/v.

In view of the above considerations, the bisulfite concentration was set at 0.5% w/w (0.048M sodium sulfite) of the aqueous phase for Examples 23 to 26, giving a slight molar excess of bisulfite at 50% hydrolysis of racemic compound A, assuming that all of the hydrolyzed compound A is transformed to compound C and that the 1 liter of aqueous phase is used for every 0.094 moles of racemic ester in the organic phase. The resulting conditions chosen for dispersed-phase enzyme reactions consisted of an aqueous phase consisting of 50 mM pH 8.0 sodium phosphate buffer containing 0.5% w/w sodium bisulfite at ambient temperature, and an organic-to-aqueous phase ratio of approximately 1:10; these conditions were shown to give improved yields of the desired (2R,3S) enantiomer of compound A and to minimize the inhibitory effects of compound C. The results from these experiments are summarized in Examples 23-26 and in Table 12.

The data presented in Examples 18-19, Examples 23-26, and Tables 10-12 show that the presence of bisulfite in the aqueous phase during the enzymatic resolution of esters of 3-(4-methoxyphenyl)glycidate has a very beneficial effect on the enzymatic activity of Lipase OF, and positive effects on product yield and chemical and enantiomeric purity as well.

The effect of bisulfite anion at a total concentration of 0.093M on the stability of representative enzymes that might be used in this resolution process was determined, and results are summarized below:

| Enzyme | pH | Percent of Activity Remaining | |
|---|---|---|---|
| | | 24 hr | 48 hr |
| Palatase M[N] | 7.0 | 40.1 | 0.0 |
| Palatase M | 8.0 | 10.4 | 0.0 |
| Lipase MAP[A] | 7.0 | 79.4 | 0.0 |
| Lipase MAP | 8.0 | 40.1 | 0.0 |
| Lipase OF[M] | 7.0 | 85.1 | 32.2 |
| Lipase O[F] | 8.0 | 74.5 | 28.9 |
| Lipase p[A] | 8.0 | 98.1 | 95.2 |

[A]Amano International Enzyme Co.
[M]Meito Sangyo
[N]Novo Industries

The above results suggest that all enzymes are not equivalent in terms of their stability in the presence of bisulfite anion. Additional evidence is shown in Table 13, which summarizes results from Example 27. When compared against the results shown in Table 10 for Lipase OF in the presence of bisulfite anion, it becomes clear that sulfite did not enhance the catalytic activity of Palatase M.

In order to reduce the deleterious effect that bisulfite may have on certain enzymes, it is possible to add the bisulfite to the aqueous phase continuously to the aqueous phase as a function of the amount of ester that has been reacted as opposed to charging all of the bisulfite-containing species to the aqueous phase at the beginning of the reaction. That is, it is within the scope of the present invention to gradually add the amount of bisulfite needed to react with the amount of aldehyde being generated by the enzymatic reaction. This form of bisulfite addition has the advantage of keeping to a minimum the amount and concentration of free bisulfite that is available to interact with the enzyme.

5.4. Examples Pertinent of Bisulfite Utilization

Several examples of the practice of the invention and elements thereof follow. These examples are meant to illustrate more fully the nature of the present invention without acting as a limitation upon its scope.

5.4.0. Resolution of trans-3-(4-Methoxyphenyl)glycidic Acid Methyl Ester in a Multiphase Enzyme Membrane Reactor

5.4.1. Example 18—Resolution of trans-3-(4-Methoxyphenyl)glycidic Acid Methyl Ester in a Multiphase Enzyme Membrane Reactor in the Absence of Bisulfite The enzymatic resolution of Example 18A was conducted in the type multiphase/extractive enzyme membrane reactor described above. The membrane was activated with 10 grams of Lipase OF. The membrane activation procedure is described by Matson in U.S. Pat. No. 4,795,704 and in U.S. patent application Ser. No. 912,595, filed Oct. 1, 1986 and entitled "Method and Apparatus for Catalyst Containment in Multiphase Membrane Reactor System." The organic phase was prepared by dissolving 78 grams (0.375 moles) of a racemic mixture of the trans 3-(4-methoxyphenyl)glycidic acid methyl ester (compound A) in 375 ml of toluene. This organic solution was then recirculated on the shell side of a hollow fiber device. Four liters of an aqueous 50 mM sodium phosphate buffer of pH 8.0 were recirculated on the lumen side of the membrane device. The pH was maintained at 8.0 by adding sodium hydroxide with a device for monitoring and maintaining a given pH, commonly known as a "pH stat".

After 11 hours the organic fluid was drained from the membrane device. To reduce losses, the membrane device was rinsed with 500 ml of fresh toluene and the two toluene fractions were then combined. The toluene was subsequently evaporated under vacuum at 65° C. To the remaining solids methanol was added so that the solids concentration would be 20% (w/w). This solution was then chilled at −20° C. for three hours. The precipitated crystals were filtered, dried, and analyzed for optical purity. These final crystals are hereby referred to as the reactor product.

The mother liquors from the crystallization were evaporated under vacuum to remove the methanol. The remaining liquid was then analyzed for ester concentration. The balance of this liquid includes the inhibitory aldehyde by-product compound C.

A second enzymatic resolution (Example 18B), conducted in the same membrane reactor still containing the same enzyme used in Example 18A, was started 13 hours after completion of the first resolution. This second reaction was stopped after 22 hours and the organic phase was processed in the same manner as in the first resolution. The results from these two resolutions are summarized in Table 10.

5.4.2. Example 19—Resolution of trans-3-(4-methoxyphenyl)glycidic Acid Methyl Ester in a Multiphase Enzyme Membrane Reactor using Sodium Bisulfite The enzymatic resolution of Example 19A was conducted in the same type of multiphase/extractive enzyme membrane reactor described above. The membrane was activated with 10 grams of Lipase OF. The membrane activation procedure is described by Matson in U.S. Pat. No. 4,795,704 and in U.S. patent application Ser. No. 912,595, filed Oct. 1, 1986 and entitled "Method and Apparatus for Catalyst Containment in Multiphase Membrane Reactor System." The organic phase was prepared by dissolving 78 grams (0.375 moles) of a racemic mixture of the trans 3-(4-methoxyphenyl)glycidic acid methyl ester (compound A) in 375 ml of toluene. This organic solution was then recirculated on the shell side of a hollow fiber device. Four liters of a pH 8.0 buffer solution containing 0.2 moles of sodium phosphate and 0.375 moles of sodium bisulfite were recirculated on the lumen side of the membrane device.

The reaction was stopped after 7.5 hours and the organic fluid was drained from the membrane device. To reduce losses, the membrane device was rinsed with 500 ml of fresh toluene and the two toluene fractions were then combined. The toluene was subsequently evaporated under vacuum at 65° C. To the remaining solids methanol was added so that the solids concentration would be 20% (w/w). This solution was then chilled at −20° C. for three hours. The precipitated crystals were filtered, dried, and analyzed for optical purity. These final crystals are hereby referred to as the reactor product.

The mother liquors from the crystallization were evaporated under vacuum to remove the methanol. The remaining liquid was then analyzed for ester concentration. The balance of this liquid includes the inhibitory aldehyde by-product compound C.

A second enzymatic resolution (Example 19B), conducted in the same membrane reactor used in Example 19A and still containing the same enzyme, was started 16 hours after completion of the first resolution. This second reaction was stopped after 7.5 hours and the organic phase was processed in the same manner as in the first resolution.

A third enzymatic resolution (Example 19C), conducted in the same membrane reactor used in Examples 19A and 19B and still containing the same enzyme, was started 16 hours after completion of the second resolution. This third reaction was stopped after 7.5 hours and the organic phase was processed in the same manner as in the first and second resolution. The results from all three resolutions are summarized in Table 10.

TABLE 10

| Example No. | 18A | 18B | 19A | 19B | 19C |
|---|---|---|---|---|---|
| Resolution No. | 1 | 2 | 1 | 2 | 3 |
| Sulfite used? | NO | NO | YES | YES | YES |
| Reaction time (hr) | 11.0 | 22.0 | 7.5 | 7.5 | 7.5 |
| Conversion (%) | 57.1 | 59.8 | 54.5 | 54.7 | 54.0 |
| Average rate of reaction (mmole/hr) | 19.5 | 10.2 | 27.3 | 27.4 | 27.0 |
| Product yield (%) | 36.4 | 35.0 | 39.2 | 38.5 | 39.1 |
| Weight of inhibitory aldehydic product recovered (g) | 18.6 | 20.9 | 1.6 | 2.9 | 1.5 |
| Enantioselectivity E | 10.9 | 14.8 | 26.6 | 19.4 | 23.9 |

Definitions

Conversion is defined as the amount of glycidate ester that was reacted, divided by the initial amount of racemic ester charged to the reactor (78 g, 0.375 moles).

Average rate of reaction is the amount of glycidate ester that was reacted divided by the total reaction time.

Product yield is the amount of resolved material isolated from the reactor (following the procedure described in Example 18) divided by the amount of racemic ester charged to the reactor (78 g, 0.375 moles).

Weight of inhibitory aldehydic product is the amount of nonester material isolated from the reactor.

5.4.3. Example 20—Enrichment of Reaction Product from Enzymatic Resolution of trans-3-(4-Methoxyphenyl)glycidic Acid Methyl Ester Using Sodium Bisulfite 50 ml of toluene containing 10 mmoles of racemic compound A were shaken with 50 mls of 0.2M sodium phosphate buffer of pH 8.0, containing 100 mgs of the commercial enzyme preparation from Amano known as Lipase MAP, for 18 hours at ambient temperature. The reaction mixture was then diluted with water to 400 mls volume, and extracted twice with 400 mls diethyl ether. The combined organic phases were then back extracted twice with 400 mls water, dried over magnesium sulphate, and evaporated to leave 1.5g (7.2 mmoles) of crude product material. The optical rotation of this material in ethanol at c=1.0 was −68.0 degrees, indicating an enantiomeric excess of 34.7%. (The value of −196.2 degrees was used as the standard for 100% enantiomeric excess of the (2R,3S) enantiomer as measured in ethanol). The crude product was then re-dissolved in 300 mls diethyl ether, and the organic solution washed twice with 100 mls of a 10% sodium bisulfite solution. The organic phase was then backwashed with water, dried over magnesium sulphate, and evaporated to leave 1.4g (6.7 mmoles) of a more pure product material. The optical rotation of this material in ethanol at c=1.0 was −117.5 degrees, indicating an enantiomeric excess of 59.9% of the desired (2R,3S) enantiomer of compound A.

5.4.4. Example 21—Recovery of trans-3-(4-methoxyphenyl)glycidic Acid Methyl Ester from Toluene using Concentrated Sodium Bisulfite 2.0 g of pure, racemic compound A were dissolved in 200 mls of diethyl ether. This organic solution was then extracted once with 250 mls of a 10% bisulfite solution, washed with 250 mls water, dried over magnesium sulphate, and evaporated to leave 1.8 g of racemic compound A, indicating a 10% loss of material. Recovery of material in the absence of the bisulfite wash was nearly quantitative.

5.4.5. Example 22—Degree of Inhibition on Representative Enzymes by Reaction Products A reaction mixture composed of 12 mls of 50 mM sodium phosphate buffer at pH 8.0 and 8 mls of a 400 mM toluene solution of pure, racemic compound A, was rapidly stirred and the reaction rate monitored by a device known as a "pH stat". A given amount of a given commercial enzyme preparation was then added to the reaction mixture, and the initial rate of hydrolysis calculated. The reaction was repeated in the presence of 1 mmole (50 mM) of compound C, in the presence of 1 mmole (50 mM) of compound D, and in the presence of 1 mmole (50 mM) of compound E. The results are tabulated in Table 11.

TABLE 11

| Enzyme | Relative Initial Rates* | | | |
|---|---|---|---|---|
| Compound(s): | A | A + C | A + D | A + E |
| Lipase OF | 1.0 | 0.63 | 1.18 | >1.50 |
| Lipase MAP | 1.0 | 0.73 | 0.99 | 1.03 |
| Lipase P | 1.0 | 1.00 | 1.07 | 1.06 |
| Palatase M | 1.0 | 0.38 | >1.0 | 0.69 |

*Note:
relative initial rates are not normalized between enzymes

5.4.6. Example 23—Resolution of trans-3-(4-Methoxyphenyl)glycidic Acid Methyl Ester Using Sodium Bisulfite 400 mls of a solution of 50mM sodium phosphate buffer at pH 8.0 and containing 0.5% weight by volume sodium bisulfite, was stirred together with 42.5 mls of toluene containing 7.8 g (37.5mmoles, approx. 0.88M) in a 600 ml beaker, and monitored by a pH stat equipped to titrate the reaction with sodium hydroxide in order to hold the pH at 8.0. To this were added 100 mgs of the commercial preparation of Lipase OF, and the reaction allowed to proceed for 90 minutes. The reaction mixture was then poured into a separatory funnel, extracted twice with 400 mls of diethyl ether, and the combined organic phases dried over magnesium sulphate. Evaporation of the ether left compound A enriched in the desired (2R,3S) enantiomer. This crude product was then re-crystallized once in the conventional manner from a minimal volume of hot methanol, and the re-crystallized products recovered by filtration. The enantiomeric excess of the various crude and re-crystallized products were measured in ethanol at c=1.0, using the standard value of −196.2 degrees as 100% enantiomeric excess of the (2R,3S) enantiomer. The percentage yield listed is the yield of product expressed as a percent of the original amount of substrate. The percentage yield of the (2R,3S) enantiomer is expressed as the percentage of the amount of this enantiomer originally present in the racemic substrate, and is the product of percent yield times percent e.e. The results are summarized in Table 12.

5.4.7. Example 24—Resolution of trans-3-(4-methoxyphenyl)glycidic Acid Methyl Ester in the absence of Sodium Bisulfite 400 mls of a solution of 50 mM sodium phosphate buffer at pH 8.0 was stirred together with 42.5 mls of toluene containing 7.8 g (37.5 mmoles, approx. 0.88M) in a 600 ml beaker, and monitored by a pH stat equipped to titrate the reaction with sodium hydroxide in order to hold the pH at 8.0. To this were added 100mgs of the commercial preparation of Lipase OF, and the reaction allowed to proceed for 90 minutes. The reaction mixture was then poured into a separatory funnel, extracted twice with 400 mls of diethyl ether, and the combined organic phases dried over magnesium sulphate. Evaporation of the ether left compound A enriched in the desired (2R,3S) enantiomer. This crude product was then re-crystallized once in the conventional manner from a minimal volume of hot methanol, and the re-crystallized products recovered by filtration. The enantiomeric excess of the various crude and re-crystallized products were measured in ethanol at c=1.0, using the standard value of −196.2 degrees as 100% enantiomeric excess of the (2R,3S) enantiomer. The percentage yield listed is the yield of product expressed as a percent of the original amount of substrate. The percentage yield of the (2R,3S) enantiomer is expressed as the percentage of the amount of this enantiomer originally present in the racemic substrate, and is the product of percent yield times percent e.e. The results are summarized in Table 12.

5.4.8. Example 25—Resolution of trans-3-(4-methoxyphenyl)glycidic Acid Methyl Ester using Sodium Bisulfite and Extended Reaction Time 400 mls of a solution of 50 mM sodium phosphate buffer at pH 8.0 and containing 0.5% weight by volume sodium bisulfite, was stirred together with 42.5 mls of toluene containing 7.8 g (37.5 mmoles, approx. 0.88M) in a 600 ml beaker, and monitored by a pH stat equipped to titrate the reaction with sodium hydroxide in order to hold the pH at 8.0. To this were added 100 mgs of the commercial preparation of Lipase OF, and the reaction allowed to proceed for 4 hours. The reaction mixture was then poured into a separatory funnel, extracted twice with 400 mls of diethyl ether, and the combined organic phases dried over magnesium sulphate. Evaporation of the ether left compound A enriched in the desired (2R,3S) enantiomer. This crude product was then re-crystallized once in the conventional manner from a minimal volume of hot methanol, and the re-crystallized products recovered by filtration. The enantiomeric excess of the various crude and re-crystallized products were measured in ethanol at c=1.0, using the standard value of −196.2 degrees as 100% enantiomeric excess of the (2R,3S) enantiomer. The percentage yield listed is the yield of product expressed as a percent of the original amount of substrate. The percentage yield of the (2R,3S) enantiomer is expressed as the percentage of the amount of this enantiomer originally present in the racemic substrate, and is the product of percent yield times percent e.e. The results are summarized in Table 12.

5.4.9. Example 26—Resolution of trans-3-(4-methoxyphenyl)glycidic Acid Methyl Ester using Sodium Bisulfite in a Larger Scale 1200 mls of a solution of 50 mM sodium phosphate buffer at pH 8.0 and containing 0.5% weight by volume sodium bisulfite, was stirred together with 127.5 mls of toluene containing 23.4 g (112.5 mmoles, approx. 0.88M) in a 2000 ml beaker, and monitored by a pH stat equipped to titrate the reaction with sodium hydroxide in order to hold the pH at 8.0. To this were added 300 mgs of the commercial preparation of Lipase OF, and the reaction was allowed to proceed for 90 minutes. The reaction mixture was then poured into a separatory funnel, extracted twice with 1200 mls of diethyl ether, and the combined organic phases dried over magnesium sulphate. Evaporation of the ether left compound A enriched in the desired (2R,3S) enantiomer. This crude product was then re-crystallized once in the conventional manner from a minimal volume of hot methanol, and the re-crystallized products recovered by filtration. The enantiomeric excess of the various crude and re-crystallized products were measured in ethanol at c=1.0, using the standard value of −196.2 degrees as 100% enantiomeric excess of the (2R,3S) enantiomer. The percentage yield listed is the yield of product expressed as a percent of the original amount of substrate. The percentage yield of the (2R,3S) enantiomer is expressed as the percentage of the amount of this enantiomer originally present in the racemic substrate, and is the product of percent yield times percent e.e. The results are summarized in Table 12.

TABLE 12

| Example | Recovered Compound A | % yield | $[\alpha]_D$ (EtOH) | % e.e. | % (2R, 3S) |
|---|---|---|---|---|---|
| 23 | 3.4 g | 43.6% | −193.0 | 98% | 42.7% |
| 24 | 3.4 g | 43.0% | −162.0 | 82% | 35.2% |
| 25 | 3.1 g | 39.7% | −182.4 | 93% | 36.9% |
| 26 | 11.0 g | 47.0% | −161.7 | 82% | 38.5% |

5.4.10. Example 27—Resolution of trans-3-(4-Methoxyphenyl)glycidic Acid Methyl Ester in a Multiphase Enzyme Membrane Reactor Using Palatase M The enzymatic resolution of Example 27A was conducted in the same type of multiphase/extractive enzyme membrane reactor described above. The membrane was activated with 150 ml of Palatase M solution (Novo). The membrane activation procedure is described by Matson in U.S. Pat. No. 4,795,704 and in U.S. patent application Ser. No. 912,595, filed Oct. 1, 1986 and entitled "Method and Apparatus for Catalyst Containment in Multiphase Membrane Reactor System." The organic phase was prepared by dissolving 78 grams (0.375 moles) of a racemic mixture of the trans-glycidic methyl ester in 375 ml of toluene. This organic solution was then recirculated on the shell side of a hollow fiber device. Four liters of a pH 8.0 buffer solution containing 0.2 moles of sodium phosphate and 0.375 moles of sodium bisulfite were recirculated on the lumen side of the membrane device.

After 7.5 hours the organic fluid was drained from the membrane device. To reduce losses, the membrane device was rinsed with 500 ml of fresh toluene and the two toluene fractions were then combined. The toluene was subsequently evaporated under vacuum at 65° C. To the remaining solids methanol was added so that the solids concentration would be 20% (w/w). This solution was then chilled at −20° C. for three hours. The precipitated crystals were filtered, dried, and analyzed for optical purity. These final crystals are hereby referred to as the reactor product.

The mother liquors from the crystallization were evaporated under vacuum to remove the methanol. The remaining liquid was then analyzed for ester concentration. The balance of this liquid is assumed to be the inhibitory aldehydic product.

A second enzymatic resolution (Example 27B), conducted in the same membrane reactor of Example 27A and still containing the same enzyme, was started 16 hours after completion of the first resolution. This second reaction was stopped after 7.5 hours and the organic phase was processed in the same manner as in the first resolution.

A third enzymatic resolution (Example 27C), conducted in the same membrane reactor of Examples 27A and 27B and still containing the same enzyme, was started 16 hours after completion of the second resolution. This third reaction was stopped after 7.5 hours and the organic phase was processed in the same manner as in the first and second resolution. The results from all three resolutions are summarized in Table 13.

TABLE 13

| Example No. | 27A | 27B | 27C |
|---|---|---|---|
| Sulfite used? | YES | YES | YES |
| Reaction time (hr) | 7.5 | 7.5 | 7.5 |
| Conversion | 51.8 | 47.7 | 41.6 |
| Average rate of reaction (mmole/hr) | 25.9 | 23.8 | 20.8 |
| Product yield (%) | 39.2 | 40.4 | 35.13 |
| Enantioselectivity E | 26.0 | 27.8 | 10.8 |

The present invention is not intended to be limited in scope by the above experiments or by the reactants, solvents, solutions, membranes, or catalysts used since each is intended merely as an illustration of the invention. In addition, functional equivalents of the claimed methods utilized and set forth herein are intended to be within the scope of this invention. Indeed, various modifications of the invention, in addition to those shown and described herein, will become apparent to those skilled in the art from the foregoing description and accompanying specification. Such modifications are intended to fall within the scope of the appended claims.

We claim:

1. A method for resolving a racemic mixture of a trans-glycidic acid ester compound of the formula II;

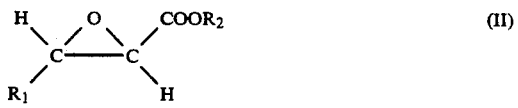

wherein $R_1$ is selected from the group consisting of phenyl or substituted phenyl and $OR_2$ in a group derived from an alcohol, the method comprising:
(a) providing an organic solution comprising a water-immiscible organic solvent and a racemic compound of formula II present as a mixture of a first and a second stereoisomer; and
(b) contacting said organic solution of first and second stereoisomers with an aqueous mixture comprising water, a suitable hydrolytic enzyme, and a bisulfite anion, wherein said enzyme catalyzes the stereoselective hydrolysis of said first stereoisomer to form an alcohol compound of the formula $R_2OH$ and an aldehyde by-product of the formula III;

wherein said aldehyde of formula III reacts with said bisulfite anion to form a water-soluble adduct of the formula IV

2. A method for resolving a racemic mixture of a trans-glycidic acid ester compound of the formula II;

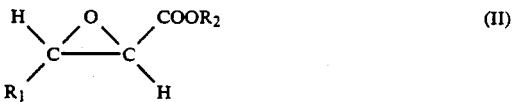

wherein $R_1$ is selected from the group of phenyl or substituted phenyl and $OR_2$ is a group derived from an alcohol, the method comprising:
(a) providing an organic solution comprising a water-immiscible organic solvent and a racemic compound of formula II present as a mixture of a first and a second stereoisomer to a first side of a membrane; and (b) providing to a second side of said membrane an aqueous mixture comprising water, a suitable hydrolytic enzyme, and bisulfite anion, wherein said enzyme catalyzes the stereoselective hydrolysis of said first stereoisomer to form an alcohol compound of the formula $R_2OH$ and an aldehyde by-product of the formula III

$R_1$—$CH_2$—CHO        (III)

wherein said aldehyde of formula III reacts with said bisulfite anion to form a water-soluble adduct of the formula IV

$R_1$—$CH_2$—CHOH—$SO_3^-$.        (IV)

3. A method for resolving a racemic mixture of a compound of the formula II

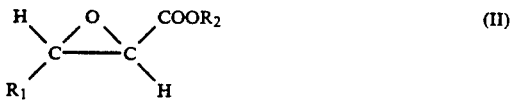

wherein $R_1$ is selected from the group of phenyl or substituted phenyl and $OR_2$ is a group derived from an alcohol, the method comprising:
  (a) providing an organic solution comprising a water-immiscible organic solvent and a racemic compound of formula I present as a mixture of a first and a second stereoisomer to one side of a membrane activated by a suitable hydrolytic enzyme that catalyzes the stereoselective hydrolysis of said first stereoisomer to form an alcohol compound of the formula $R_2OH$ and an aldehyde by-product of the formula III

$R_1$—$CH_2$—CHO        (III)

and
  (b) providing concurrently an aqueous mixture containing bisulfate anion, said aqueous mixture being substantially immiscible with said organic solution, to the opposite side of said enzyme-activated membrane, wherein said aldehyde of formula III reacts with said bisulfite anion to form a water-soluble adduct of the formula IV

$R_1$—$CH_2$—CHOH—$SO_3^-$        (IV)

4. A method for increasing the optical purity of a disastereomer of a glycidic acid ester compound of the formula I

wherein $R_1$ is selected from the group consisting of phenyl or substituted phenyl and $OR_2$ is a group derived from an alcohol, the method comprising:
  (a) providing an organic solution comprising a water-immiscible organic solvent and a diastereomer of a compound of formula I present as a mixture of a first and a second enantiomer; and
  (b) contacting said organic solution of said diastereomer with an aqueous mixture comprising water, a suitable hydrolytic enzyme, and bisulfite anion, wherein said enzyme catalyzes the enantioselective hydrolysis of said first enantiomer to form an alcohol compound of the formula $R_2OH$ and an aldehyde by-product of the formula III;

$R_1$—$CH_2$—CHO        (III)

wherein said aldehyde of formula III reacts with said bisulfite anion to form a water-soluble adduct of the formula IV

$R_1$—$CH_2$—CHOH—$SO_3^-$.        (IV)

5. A method for increasing the optical purity of a diastereomer of a glycidic acid ester compound of the formula I

wherein $R_1$ is selected from the group consisting of phenyl or substituted phenyl and $OR_2$ is a group derived from an alcohol, the method comprising:
  (a) providing an organic solution comprising a water-immiscible organic solvent and a diastereomer of a compound of formula I present as a mixture of a first and a second enantiomer to a first side of a membrane; and
  (b) providing to a second side of said membrane an aqueous mixture comprising water, a suitable hydrolytic enzyme, and bisulfite anion, wherein said enzyme catalyzes the stereoselective hydrolysis of said first enantiomer to form an alcohol compound of the formula $R_2OH$ and an aldehyde by-product of the formula III

$R_1$—$CH_2$—CHO        (III)

wherein said aldehyde of formula III reacts with said bisulfite anion to form a water-soluble adduct of the formula IV

$R_1$—$CH_2$—CHOH—$SO_3^-$        (IV)

6. A method for increasing the optical purity of a diastereomer of a glycidic acid ester compound of the formula I

wherein $R_1$ is selected from the group consisting of phenyl or substituted phenyl and $OR_2$ is a group derived from an alcohol, the method comprising:
  (a) providing an organic solution comprising a water-immiscible organic solvent and a diastereomer of a compound of formula I present as a mixture of a first and a second enantiomer to one side of a membrane activated by a suitable hydrolytic enzyme that catalyzes the enantioselective hydrolysis of said first enantiomer to form an alcohol compound of the formula $R_2OH$ and an aldehyde by-product of the formula III

$R_1$—$CH_2$—CHO        (III)

and (b) providing concurrently an aqueous mixture containing bisulfite anion, said aqueous mixture being substantially immiscible with said organic solution, to the opposite side of said enzyme-activated membrane, wherein said aldehyde of formula III reacts with said bisulfite anion to form a water-soluble adduct of the formula IV $$R_1-CH_2-CHOH-SO_3^- \quad (IV)$$

7. A method for resolving a racemic mixture of a trans-glycidic acid ester compound of the formula II

in which $R_1$ is a phenyl or substituted phenyl and $OR_2$ is a group derived from an alcohol, which method comprises:

(a) providing an organic solution comprising a water-immiscible organic solvent and a racemic compound of formula II present as a mixture of a first and a second stereoisomer; and (b) contacting said organic solution of first and second stereoisomers with an aqueous mixture comprising water, a suitable hydrolytic enzyme capable of catalyzing the stereoselective hydrolysis of said first stereoisomer, and bisulfite anion, which is capable of forming an adduct with an aldehyde of the formula III $$R_1-CH_2-CHO \quad (III)$$

which aldehyde is a by-product of said stereoselective hydrolysis, under conditions effective to provide an organic solution enriched in said second stereoisomer.

8. A process for the production of a benzothiazapene from an optically active diastereomer of a glycidic acid ester of the formula I

in which $R_1$ is a phenyl or substituted phenyl and $OR_2$ is a group derived from an alcohol, which method comprises (a) providing an organic solution comprising a water-immiscible organic solvent and a diastereomer of said glycidic acid ester present as a mixture of a first and a second enantiomer, and (b) contacting said organic solution of said diastereomer with an aqueous mixture comprising water, a suitable hydrolytic enzyme, and bisulfite anion, which is capable of forming an adduct with an aldehyde of the formula III $$R_1-CH_2-CHO \quad (III)$$

which aldehyde is a by-product of said enantioselective hydrolysis, said enzyme being capable of catalyzing the enantioselective hydrolysis of said diastereomer, under conditions effective to provide an organic solution of said optically active diastereomer of said glycidic acid ester and (c) further modifying said optically active diastereomer of said glycidic acid ester to provide said benzothiazapene.

9. The method of claims 1 or 4 wherein said organic solution and said aqueous mixture are brought into contact in step (b) by means of forming a dispersion of one of said organic solution or aqueous mixture within the other.

10. The method of claim 9 wherein said dispersion of said aqueous mixture and organic solution is contained in a reactor selected from the group consisting of a stirred-tank reactor, packed-bed reactor, and fluidized-bed reactor.

11. The method of claim 9 further comprising separating said organic solution and aqueous mixture after completion of the enzymatic hydrolysis reaction of step (b) by a process selected from the group consisting of gravitational settling, centrifugation, and membrane filtration.

12. The method of claim 9 wherein said dispersion is contacted with an adsorbent after completion of the enzymatic hydrolysis reaction of step (b) in order to deplete enzyme from said dispersion, thereby facilitating separation of the enzyme-depleted dispersion of organic solution and aqueous mixture.

13. The method of claim 11 wherein said organic solution and aqueous mixture forming said enzyme-depleted dispersion are separated by a process selected from the group consisting of gravitational settling, centrifugation, and membrane filtration.

14. The method of claims 1, 2, 4 or 5 wherein said enzyme of step (b) is immobilized on a particulate, solid-phase support.

15. The method of claims 1, 2, 3, 4, 5 or 6 wherein the aldehyde by-product of formula III is an inhibitor of the enzyme-catalyzed ester hydrolysis.

16. The method of claims 1, 2, 4 or 5 wherein the pH of said aqueous mixture ranges from a pH of about 2 to about 10.

17. The method of claim 3 or 6 wherein the pH of said aqueous solution is maintained from a pH of about 5 to about 9.

18. The method of claim 16 wherein the pH is preferably maintained between a pH of about 7.0 and a pH of about 8.5.

19. The method of claims 1, 2 or 5 wherein the concentration of said bisulfite anion in said aqueous mixture is from about 0.1% w/v to about 10% w/v.

20. The method of claim 3 or 6 wherein the concentration of said bisulfite anion in said aqueous solution is from about 0.1% w/v to about 10% w/v.

21. The method of claim 19 wherein said concentration of said bisulfite anion is preferably from about 0.5% w/v to about 5% w/v.

22. The method of claims 1, 2, 3, 5 or 6 wherein bisulfite anion is continuously added to the aqueous mixture during the reaction.

23. The method of claims 1, 2, 3, 5 or 6 wherein bisulfite anion is provided in a form selected from the group consisting of an alkali metal salt, sulfurous acid, and sulfur dioxide.

24. The method of claim 23 wherein the bisulfite anion is provided in a form selected from the group consisting of an alkali metal sulfite, an alkali metal bisulfite, and an alkali metal metabisulfite.

25. The method of claim 23 wherein the alkali metal is sodium.

26. The method of claims 1, 2, 3, 5 or 6 wherein said enzyme is not adversely inhibited by the presence of said bisulfite anion.

27. The method of claims 1, 2 or 3 wherein the stoichiometric ratio of said bisulfite anion to said first stereoisomer of formula II provided is in the range from about 0.1 to about 10.

28. The method of claim 27 wherein said stoichiometric ratio is preferably in the range of at least 1 to about 2.

29. The method of claims 1, 2, 4, or 5 wherein the ratio of said aqueous mixture volume to said organic solution volume is in the range from about 0.5 to about 10.

30. The method of claims 3 or 6 wherein the ratio of said aqueous solution volume to said organic solution volume is in the range from about 0.5 to about 20.

31. The method of claim 29 wherein said ratio is preferably in the range from about 1 to about 10.

32. The method of claims 1, 2, 3, 4, 5 or 6 wherein the substituent on said substituted phenyl group R1 is selected from the group consisting of hydroxy, methoxy, phenoxy, benzyloxy, alkoxy, aryloxy, arylalkoxy, and halide.

33. The method of claim 32 wherein said phenyl substituent or substituents occupies one or more of the ortho, meta, and para positions with respect to the glycidic ester moiety.

34. The method of claims 1, 2, 3, 4, 5 or 6 wherein $R_1$ is a 4-methoxyphenyl group.

35. The method of claims 1, 2, 3, 4, 5 or 6 wherein $R_2$ is selected from the group consisting of straight-chain alkyl containing from 1 to 8 carbon atoms, branched-chain alkyl containing from 3 to 8 carbon atoms, substituted alkyl, aryl, substituted aryl, and alkoxyalkyl.

36. The method of claim 35 wherein $R_2$ is an alkyl selected from the group consisting of methyl, ethyl, isopropyl, and isobutyl.

37. The method of claim 35 wherein $R_2$ is an alkoxyalkyl selected from the group consisting of methoxyethyl and ethoxyethyl.

38. The method of claim 35 wherein $R_2$ is a substituted alkyl selected from the group consisting of trifluoroethyl, trichloroethyl, chloroethyl, benzyl, phenylethyl, and naphthylmethyl.

39. The method of claim 35 wherein $R_2$ is an aryl selected from the group consisting of phenyl and naphthyl.

40. The method of claim 1 wherein said hydrolytic enzyme is selected from the group consisting of proteases, esterases, and lipases.

41. The method of claims 1, 2, 3, 4, 5 or 6 wherein said hydrolytic enzyme is provided in a form selected from the group consisting of purified enzyme, cell extract, cell lysate, partially purified enzyme, and whole cells.

42. The method of claims 1, 2, 3, 4, 5 or 6 wherein said hydrolytic enzyme is derived from a microorganism.

43. The method of claim 42 wherein said hydrolytic enzyme is derived from a microorganism selected from the group of genus Mucor, genus Candida, genus Pseudomonas, genus Bacillus, and genus Aspergillus.

44. The method of claim 43 wherein said hydrolytic enzyme is a protease derived from Aspergillus oryzae.

45. The method of claim 43 wherein said hydrolytic enzyme is a lipase derived from Pseudomonas fluorescens.

46. The method of claim 44 wherein said hydrolytic enzyme is Amano International Enzyme Company's Prozyme 6.

47. The method of claims 1, 2, 3, 4, 5 or 6 wherein said hydrolytic enzyme is derived from a mammal.

48. The method of claim 47 wherein said hydrolytic enzyme is selected from the group consisting of porcine liver esterase, porcine pancreatic lipase, trypsin, chymotrypsin, pancreatin, and cholesterol esterase.

49. The method of claims 1, 2, 3, 4, 5 or 6 wherein said enzymatic hydrolysis takes place at a temperature of about 15° C. to 70° C.

50. The method of claim 49 wherein said hydrolysis preferably takes place at a temperature of about 20° C. to about 45° C.

51. The method of claims 1, 2, 3, 4, 5 or 6 wherein said water-immiscible organic solvent is selected from the group consisting of toluene, tert-butyl methyl ester, hexane, cyclohexane, methyl isobutyl ketone, and ethyl acetate.

52. The method of claims 2, 3, 5 or 6 wherein the membrane is a hydrophilic membrane.

53. The method of claims 2, 3, 5 or 6 wherein the membrane is a hydrophobic membrane.

54. The method of claims 2, 3, 5 or 6 wherein the membrane is a microporous membrane.

55. The method of claim 3 or 6 wherein the enzyme which activates said membrane is deposited as a gel layer on the surface of said membrane.

56. The method of claim 3 or 6 wherein the enzyme which activates said membrane is located within said membrane.

57. The method of claim 3 or 6 wherein the enzyme which activates said membrane is contained within the pore spaces of an asymmetric, microporous membrane.

58. The method of claim 3 or 6 wherein the enzyme which activates said membrane is adsorbed on said membrane on the pore wall surfaces of said membrane.

59. The method of claim 3 or 6 wherein the enzyme which activates said membrane is entrapped within a polymeric gel within the pores of said membrane.

60. The method of claim 3 or 6 wherein the enzyme which activates said membrane is covalently coupled to the pore wall surfaces of said membrane.

61. The method of claim 3 or 6 wherein the enzyme which activates said membrane is crosslinked within the pore spaces of said membrane.

62. The method of claim 3 or 6 wherein the enzyme which activates said membrane is crosslinked on the pore wall surfaces of said membrane.

63. The method of claims 2, 3, 5 or 6 wherein the membrane form is selected from the group consisting of flat sheet, hollow fiber, and tube.

64. The method of claims 2, 3, 5 or 6 wherein the membrane is constructed of material selected from the group consisting of regenerated cellulose, the esters of cellulose, polyacrylonitrile, polyacrylonitrile copolymers, polyurethane-containing copolymers, polyarylsulfones, polyarylethersulfones, polyarylsulfone blends, polyarylethersulfone blends, polyvinylidene fluoride, polytetrafluoroethylene, polyvinylalcohol, aliphatic polyamides, aromatic polyamides, polyimides, polyetherimides, polyesters, polycarbonates, polyolefins, polybenzimidazole and polybenzimidazolone.

65. The method of claim 64 wherein the membrane is a skinned, microporous membrane.

66. The method of claims 1, 2, 3, 4, 5 or 6 wherein said reaction is conducted in a batch-wise manner.

67. The method of claims 1, 2, 3, 4, 5 or 6 wherein said reaction is conducted in a continuous manner.

68. The method of claims 1, 2 or 3 which further comprises isolating from said organic solution after the stereoselective enzymatically-catalyzed hydrolysis step the second stereoisomer.

69. The method of claims 1, 2 or 3 which further comprises isolating from said organic solution after the stereoselective enzymatically-catalyzed hydrolysis step said stereoisomer.

70. The method of claim 17 wherein the pH is preferably maintained between a pH of about 7.0 and a pH of about 8.5.

71. The method of claim 20 wherein said concentration of said bisulfite anion is preferably from about 0.5% w/v to about 5% w/v.

72. The method of claim 24 wherein the alkali metal is sodium.

73. The method of claim 30 wherein said ratio is preferably in the range from about 1 to about 10.

74. The method of claims 4, 5 or 60 which further comprises isolating from said organic solution after the enantioselective enzymatically-catalyzed hydrolysis step said diastereomer having a higher proportion of said second enantiomer.

75. The method of claims 4, 5 or 6 which further comprises isolating from said organic solution after the enantioselective enzymatically-catalyzed hydrolysis step said second enantiomer.

76. The method of claim 1 or 4 which further comprises recovering said enzyme from said aqueous mixture.

77. The method of claims 1, 2, 3, 4, 5 or 6 wherein $R_2$ is a methyl group.

78. The method of claims 4, 5 or 6 wherein said diastereomer is a trans-glycidic acid ester compound of formula I.

79. The method of claims 4, 5 or 6 wherein said diastereomer is trans-3-(4-methoxyphenyl)glycidic acid methyl ester.

80. The method of claim 79 wherein said first enantiomer is (2S,3R)-trans-3-(4-methoxyphenyl)glycidic acid methyl ester.

81. The method of claim 79 wherein said second enantiomer is (2R,3S)-trans-3-(4-methoxyphenyl)glycidic acid methyl ester.

82. The method of claims 1, 2 or 3 wherein said first and second stereoisomer are tans-glycidic acid ester compound of formula I.

83. The method of claims 1, 2 or 3 wherein said first and second stereoisomer are trans-3-(4-methoxyphenyl)glycidic acid methyl ester.

84. The method of claim 83 wherein said first stereoisomer is (2S,3R)-trans-3-(4-methoxyphenyl)glycidic acid methyl ester.

85. The method of claim 83 wherein said second stereoisomer is (2R,3S)-trans-3-(4-methoxyphenyl)glycidic acid methyl ester.

86. The method of claims 1, 2, 3, 4, 5 or 6 wherein said enzyme is an esterase.

87. The method of claim 44 wherein said hydrolytic enzyme is a lipase from genus Candida.

88. The method of claim 43 wherein said hydrolytic enzyme is a lipase from Candida cylindracea.

89. The method of claim 87 wherein said hydrolytic enzyme is Meito Sangyo Company's Candida Lipase-OF.

90. The method of claims 1, 2, 3, 4, 5 or 6 wherein said water-immiscible organic solvent is a water-immiscible aromatic solvent.

91. The method of claims 1, 2, 3, 4, 5 or 6 wherein said water-immiscible organic solvent is toluene.

92. The method of claim 1, 2 or 3 which further comprises separating said organic solution containing said second stereoisomer from said aqueous mixture after the enzymatically-catalyzed stereoselective hydrolysis step.

93. The method of claim 1, 2 or 3 which further comprises separating said aqueous mixture containing said water-soluble adduct from said organic solution after the enzymatically-catalyzed stereoselective hydrolysis step.

94. The method of claim 4, 5 or 6 which further comprises separating said organic solution containing said second enantiomer from said aqueous mixture after the enzymatically-catalyzed enantioselective hydrolysis step.

95. The method of claim 4, 5 or 6 which further comprises separating said aqueous mixture containing said water-soluble adduct from said organic solution after the enzymatically-catalyzed enantioselective hydrolysis step.

96. The method of claim 1, 2, 3 or 7 which further comprises utilizing said second stereoisomer to prepare diltiazem.

97. The method of claim 1, 2, 3 or 7 in which said aldehyde or adduct thereof is utilized to prepare phenylacetic acid or a substituted phenylacetic acid.

98. The method of claim 2 or 7 in which said carbonyl adduct-forming agent is bisulfite.

99. The method of claim 2 or 7 in which the adduct formed is a sulfite salt.

100. The process of claim 8 in which step (c) includes allowing said optically active diastereomer of said glycidic acid ester to react with a nucleophile.

101. The process of claim 100 in which said nucleophile is an aminothiophenol or nitrothiophenol.

102. The process of claim 100 in which said reaction between said optically active diastereomer of said glycidic acid ester and said nucleophile is carried out in the presence of a Lewis acid.

103. The process of claim 8 in which said optically active compound is a diltiazem.

104. The method of claim 1, 2, 3 or 7 in which said aldehyde of the formula III is phenylacetaldehyde or a substituted phenylacetaldehyde.

105. The method of claim 104 in which said aldehyde of the formula III is a 4-methoxyphenylacetaldehyde.

106. The method of claim 97 in which said substituted phenylacetic acid is 4-methoxyphenylacetic acid.

* * * * *